United States Patent
Wachtel et al.

(10) Patent No.: US 7,414,720 B2
(45) Date of Patent: Aug. 19, 2008

(54) MEASURING PARTICLE SIZE DISTRIBUTION IN PHARMACEUTICAL AEROSOLS

(76) Inventors: Herbert Wachtel, Im Bangert 18, Bingen (DE) 55411; Jochen Ziegler, Viernheimer Weg 3, Heidelberg (DE) 69123; Dieter Hochrainer, Josef-Knettel-Str. 4a, Bingen am Rhein (DE) 55411; Georg Boeck, Benjamin-Franklin-Str. 8, Mainz (DE) 55122; Hubert Hoelz, Am Sonnenhang, Oberheimbach (DE) 55413; Christian Scheffler, Binger Str. 50, Ingelheim (DE) 55218; Christoph Kreher, Seerobenstr. 11, Wiesbaden (DE) 65195

( * ) Notice: Subject to any disclaimer, the term of this patent is extended or adjusted under 35 U.S.C. 154(b) by 130 days.

(21) Appl. No.: 11/551,881

(22) Filed: Oct. 23, 2006

(65) Prior Publication Data

US 2007/0122349 A1    May 31, 2007

Related U.S. Application Data

(63) Continuation-in-part of application No. 11/003,167, filed on Dec. 3, 2004, now abandoned, and a continuation-in-part of application No. 10/202,572, filed on Jul. 24, 2002, now Pat. No. 7,247,496.

(30) Foreign Application Priority Data

Jul. 27, 2001    (DE) ............... 101 36 555
Dec. 23, 2003    (EP) ............... 03029721

(51) Int. Cl.
    *G01N 15/02* (2006.01)
(52) U.S. Cl. .................... 356/336; 356/335
(58) Field of Classification Search .......... 356/335, 356/336

See application file for complete search history.

(56) References Cited

U.S. PATENT DOCUMENTS

| 3,990,797 | A  | * | 11/1976 | Neukermans et al. ....... 356/521 |
| 6,681,768 | B2 | * | 1/2004  | Haaije de Boer et al. ....... 128/203.15 |
| 2003/0015195 | A1 | * | 1/2003 | Haaije de Boer et al. ....... 128/203.15 |
| 2003/0054566 | A1 | * | 3/2003 | Hochrainer et al. ......... 436/181 |
| 2005/0142665 | A1 | * | 6/2005 | Wachtel et al. ............... 436/181 |

* cited by examiner

*Primary Examiner*—Roy M Punnoose
(74) *Attorney, Agent, or Firm*—Mary-Ellen M. Devlin; Alan R. Stempel; Philip I. Datlow

(57) ABSTRACT

Disclosed herein are methods for measuring the particle size distribution of a pharmaceutical aerosol, including methods utilizing laser diffraction.

4 Claims, 19 Drawing Sheets

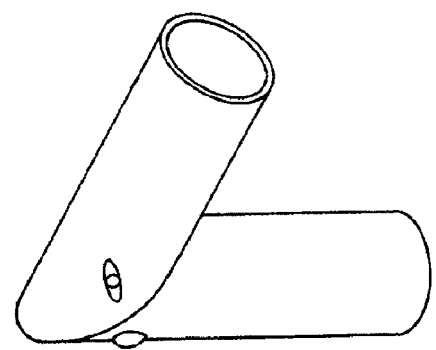
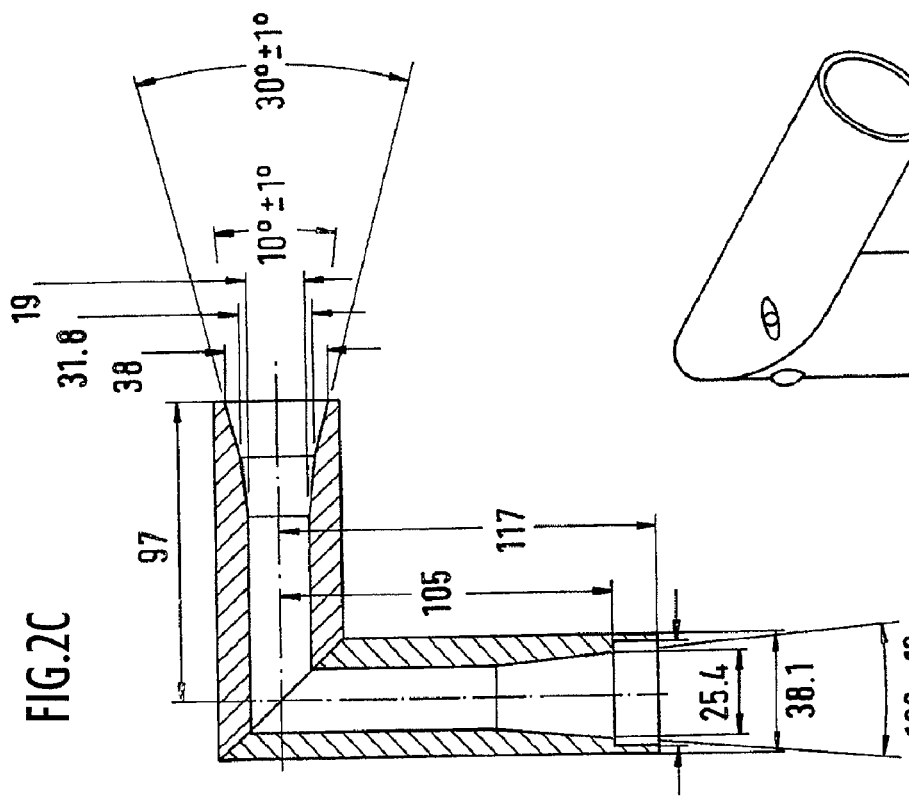
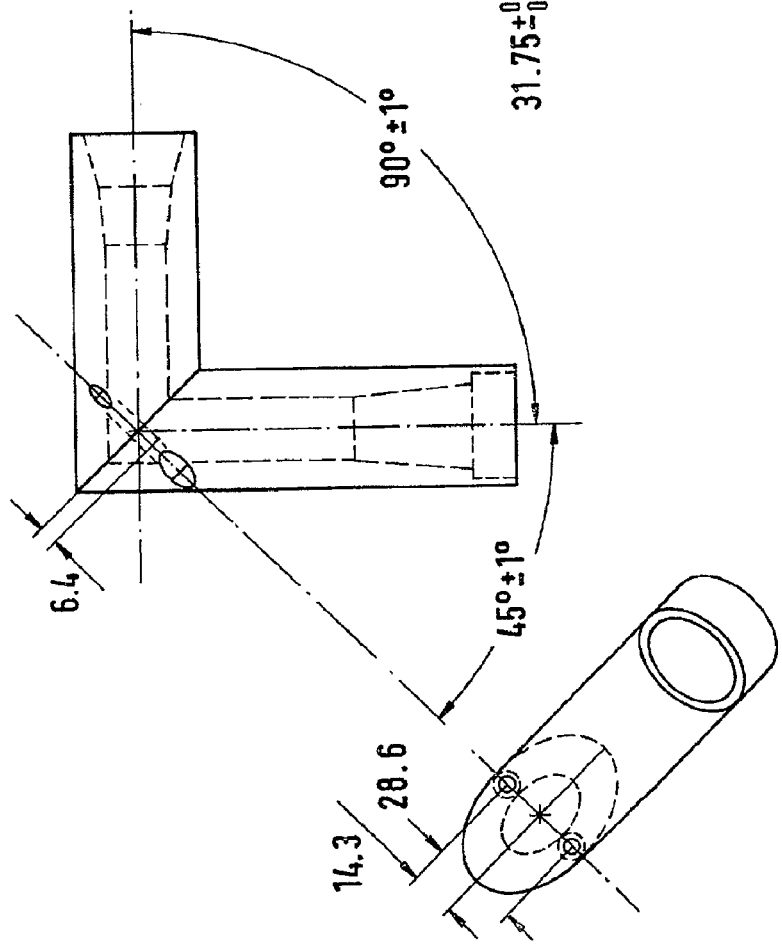

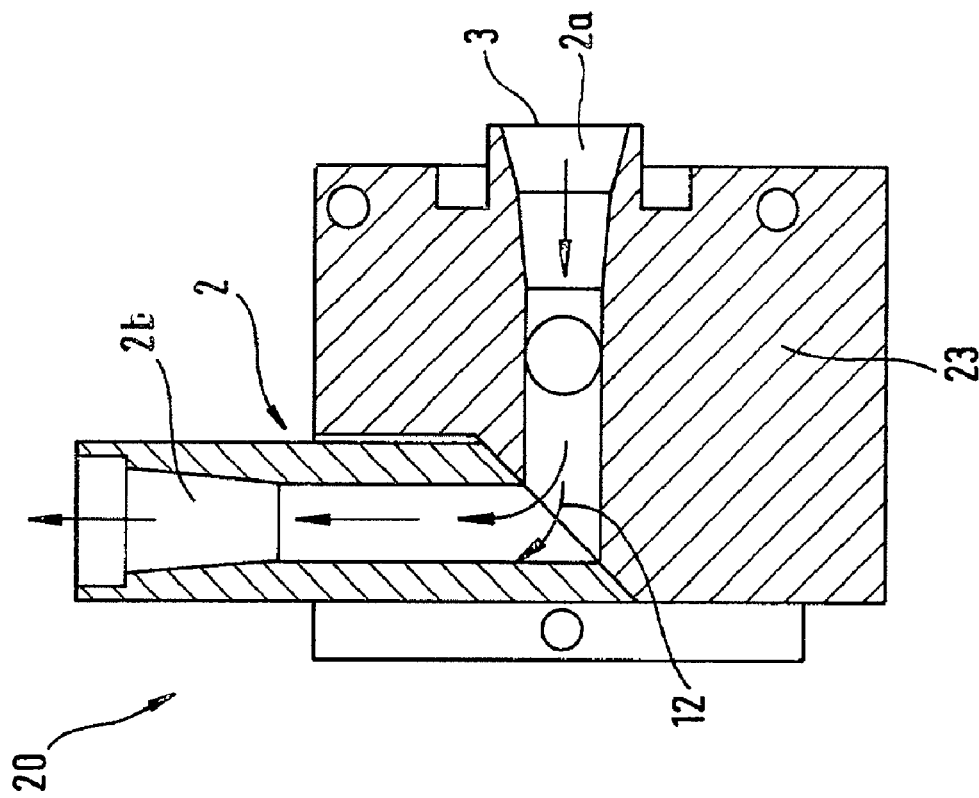
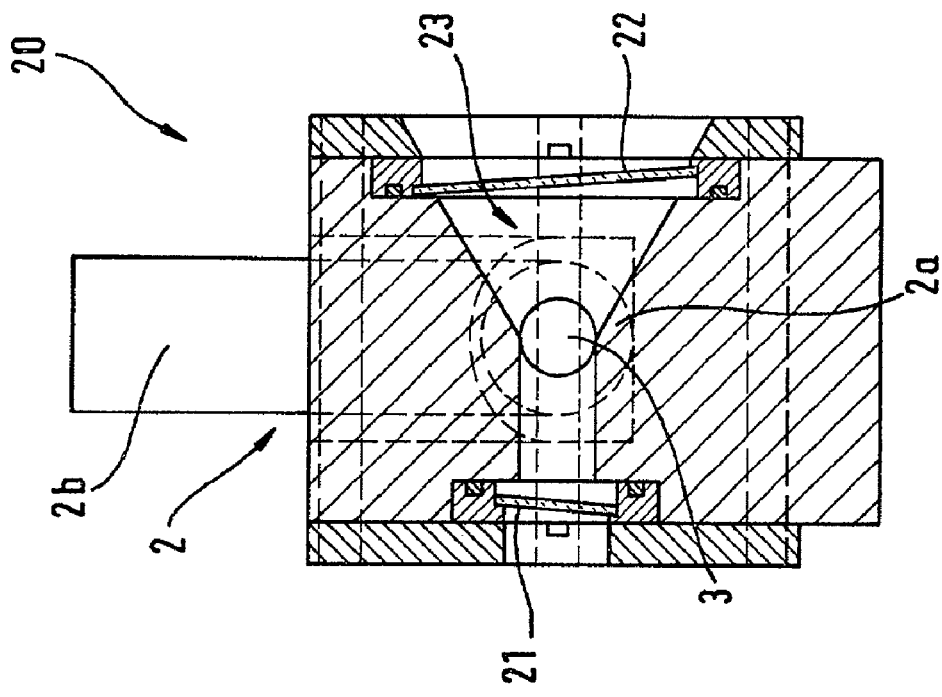
FIG.6A
FIG.6B

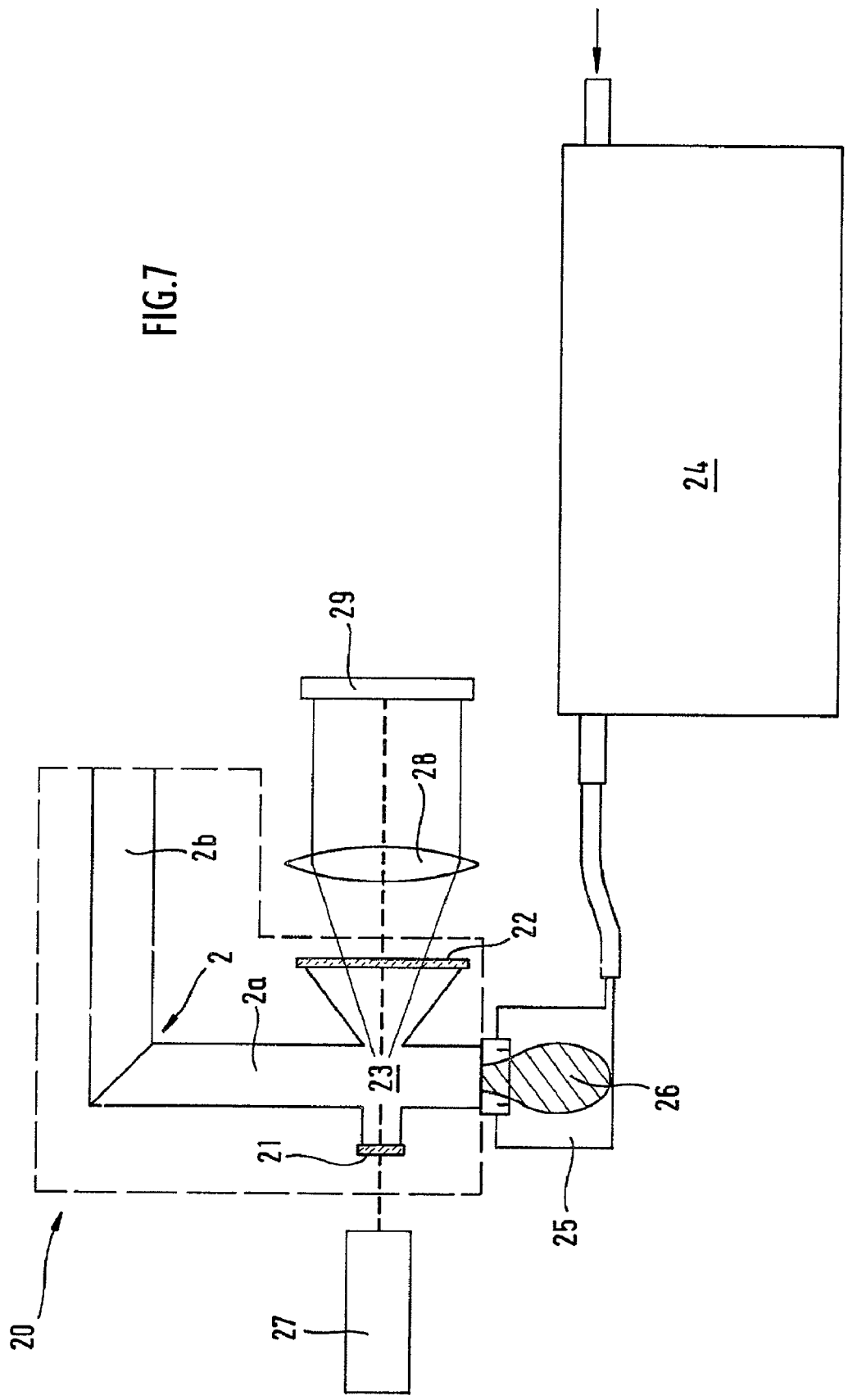

laser    beam         aerosol    collection      detector
         expander     sample     lens

FIG.8

FIG.10A
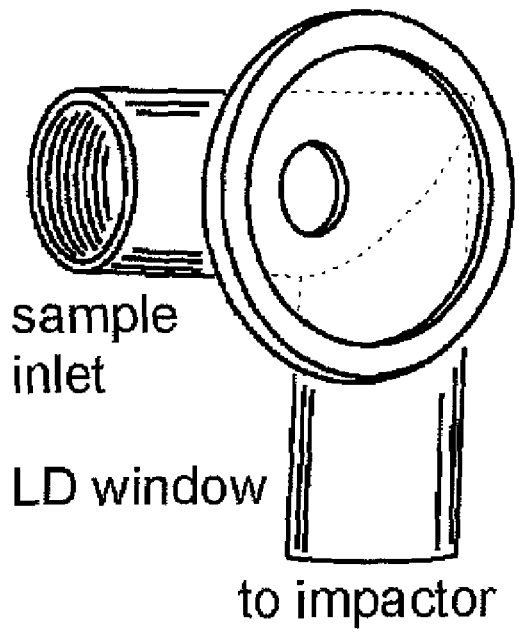
sample inlet
LD window
to impactor
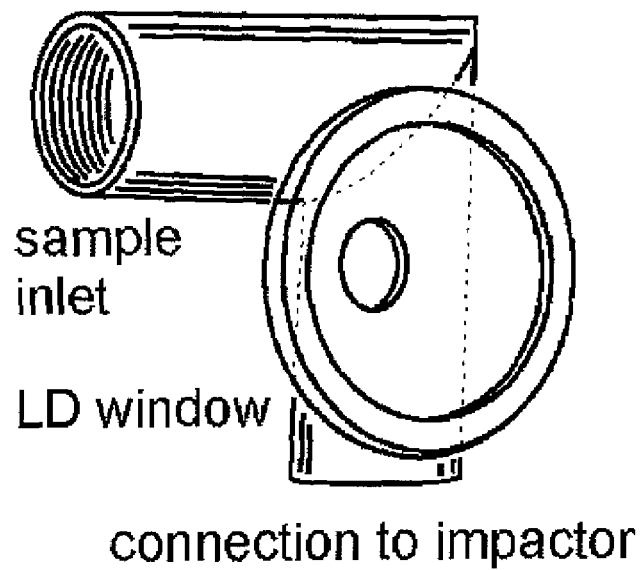
sample inlet
LD window
connection to impactor
FIG.10B

MEASURING PARTICLE SIZE DISTRIBUTION IN PHARMACEUTICAL AEROSOLS

CROSS REFERENCE TO RELATED APPLICATIONS

This application is a continuation-in-part of U.S. patent application Ser. No. 11/003,167, filed on Dec. 3, 2004, which claims priority under 35 U.S.C. §119 from European Patent Application No. 03029721.2, filed on Dec. 23, 2003. This application is further a continuation-in-part of U.S. patent application Ser. No. 10/202,572, filed on Jul. 24, 2002, which claims priority under 35 U.S.C. §119 from German Patent Application No. 101 36 555, filed on Jul. 27, 2001. The disclosures of the above-mentioned patent applications are incorporated herein by reference in their entireties.

FIELD OF THE INVENTION

The invention relates to processes for determining the size distribution of the particles contained in an aerosol, in particular particles of a pharmaceutical formulation, and to apparatuses for carrying out such processes.

BACKGROUND

Within the scope of the invention the term "pharmaceutical substance" refers to the active ingredient of a medicament which is usually also known as a drug or active substance.

The term "pharmaceutical formulation" is to be interpreted broadly, to cover formulations in the form of solutions, suspensions and powders, in particular. In a solution formulation the pharmaceutical substance is dissolved in a solvent, whereas in a suspension or powder formulation the pharmaceutical substance is present in solid form. Whereas in a suspension formulation it is mixed with a suspension agent and the pharmaceutical substance is contained in this suspension agent in the form of suspended particles, a powder formulation does not have any solvent or suspension agent in this sense but is present to some extent in pure form, as a pure powder.

A solution formulation is prepared and metered using an atomiser or nebuliser, preferably a nebuliser, in which a quantity of less than 100 ml, preferably less than 50 ml, preferably less than 20 ml of the formulation is prepared.

An apparatus of this kind for propellant-free nebulising of a metered amount of the abovementioned pharmaceutical formulations is described in detail, for example, in International Patent Application WO 91/14468 "Atomizing Device and Method" and also in WO 97/12687, FIGS. 6a and 6b. In a nebuliser of this kind a pharmaceutical formulation is converted into an aerosol by the use of high pressure, up to 500 bar, the particles introduced having a diameter of less than 100 µm, preferably less than 20 µm.

Apart from this device, other inhalers known from the prior art may also be used in the process according to the invention, such as the MDI (metered dose inhaler) or powder inhalers such as the one known by the trademark HandiHaler®, for example.

In nebulisers of this kind the formulations are stored in a reservoir and for this reason the formulations used must be sufficiently stable when stored.

It is essential in the pharmaceutical industry to measure the particle size distributions of aerosols in order to assess the characteristics of deposition in the lungs and bronchial region, as will be shown hereinafter.

In a number of applications, particularly in the case of diseases of the lungs and bronchial region, the pharmaceutical substance is provided in the form of an inhalable medicament. The pharmaceutical formulation is atomised to form an aerosol. The aerosol thus produced can then be transported in a carrier medium, e.g. air.

For example, when an asthma spray is used, a pharmaceutical formulation stored in an atomiser is finely atomised through a nozzle, by brief actuation, and introduced into the ambient air breathed in by the patient, this ambient air acting as the carrier medium. The air enriched with the pharmaceutical formulation forms an aerosol, which is inhaled.

Inhalable preparations demand a certain form for the medicament. As a rule, micronised pharmaceuticals or active substances in solid form are used. However, in theory, the drug may be present in liquid or solid form, e.g. as a powder, while solid particles do not dissolve in the solvent in the traditional sense or are present in pure form.

To ensure that the pharmaceutical substance is capable of being inhaled, stringent demands are made of the particle size, particle size distribution, morphology, stability and flow characteristics.

As a rule, not all the inhaled dose of the pharmaceutical substance reaches the lungs but only part of this dose. The amount of the composition which actually enters the lungs is critically influenced by the particle size. For this reason, particles with a diameter of less than 20 µm, preferably less than 5 µm and greater than 0.3 µm are preferred.

The diameter of the particle should fall within the range specified and should additionally have the narrowest possible size distribution. Larger particles are deposited too early, in the upper respiratory tract, when breathed in, whereas smaller particles are not deposited in the lungs and are breathed out again.

For example, when an asthma spray is used, a pharmaceutical formulation stored in an atomiser is finely atomised through a nozzle, by brief actuation, and introduced into the ambient air breathed in by the patient, this ambient air acting as the carrier medium. The air enriched with the pharmaceutical formulation forms an aerosol, which is inhaled.

To ensure that the pharmaceutical substance is capable of being inhaled, stringent demands are made of the particle size, particle size distribution, morphology, stability and flow characteristics.

As a rule, not all the inhaled dose of the pharmaceutical substance reaches the lungs but only part of this dose. The amount of the composition which actually enters the lungs is critically influenced by the particle size. For this reason, particles with a diameter of less than 20 µm, preferably less than 5 µm and greater than 0.3 µm are preferred.

The diameter of the particle should fall within the range specified and should additionally have the narrowest possible size distribution. Larger particles are deposited too early, in the upper respiratory tract, when breathed in, whereas smaller particles are not deposited in the lungs and are breathed out again.

By the particle diameter within the scope of the present invention is meant the aerodynamic particle diameter, which is defined as the equivalent diameter of a sphere with a density of 1 $g/cm^3$ which has the same sedimentation speed in air as the particle under investigation.

Against this background it is easily understandable that the pharmaceutical industry has a need for a process which can be used to determine the particle size distribution of aerosols.

However, the legislators, and particularly the health authorities, also demand accurate knowledge of the dose that is actually administered, i.e. the proportion of the total dose inhaled which is deposited in the lungs and bronchial region.

Moreover, apart from the absolute quantity administered, the size distribution affects the bioavailability of the pharmaceutical substance in that, although the absolute amounts are the same, a large number of small particles have a different bioavailability from a small number of large particles.

According to the prior art, three conventional methods are used to determine the particle size distribution.

A first, widely used method of determining particle size distribution is the so-called impaction method using the Andersen cascade impactor. The cascade impactor is a standardised apparatus for carrying out a standardised measuring process, the so-called impaction method; both the process and the apparatus are described in detail in drugs manuals (cf. also European Pharmacopoeia, $3^{rd}$ Edition, Supplement 2001, 2.9.18 Preparation for inhalation).

The cascade impactor can be considered as a simplified model of the respiratory system of human beings. The aerosol is guided by means of an air stream at defined flow rate through the rectangular bend (model of the human throat) and the following impaction stages (modelling different parts of the bronchial tubes). The impaction stages consist of nozzle plates and impaction plates. The diameter of the nozzles in the nozzle plates adjusts the air stream velocity. When the aerosol stream curves to flow around the obstructing impaction surface those particles will impact that have too much inertia to follow the air stream. If the velocity of the air stream is subsequently increased by passing it through a smaller jet (decreasing the nozzle diameters), which is followed by another impaction plate, some of the particles that succeeded in passing the previous impaction stages may be unable to follow the faster moving air stream and will impact. The stepwise decrease of the jet diameters of the successive impaction stages simulates the air ducts in the lung becoming smaller at each branching.

This method is well accepted by the national medical agencies due to its simplicity and robustness. The whole system is defined and can be described by only a few parameters like the flow rate of the air stream, the number of nozzles, the jet diameter defined by the nozzle diameters of the nozzle plates, the distance of the nozzles to the impaction plates and the length of the nozzles.

FIG. 1 shows the Andersen cascade impactor in diagrammatic side view and partially in section. The cascade impactor (1) is acted upon by the aerosol which is under investigation through the inlet opening (3) of a right-angled inlet tube (2).

The inlet (2) is a standardised component which is also known as a USP throat and simulates the oropharyngeal-cervical cavity in humans. To illustrate the USP throat, Figure 2.9.17-7 (induction port) is reproduced in FIGS. 2a to 2d.

FIG. 2d shows the USP throat in perspective view, while FIGS. 2a to 2c serve to illustrate the dimensions envisaged. FIGS. 2a to 2d are intended to give an overall impression of the USP throat and show that it is a component with an extremely detailed specification, leaving no leeway for the manufacturer or user.

As with the pharmaceutical formulation administered to the patient with the ambient air breathed in, with which it forms an aerosol, is passed through the oral and pharyngeal cavities into the windpipe and from there is passed into the lungs to the bronchi, in the Andersen cascade impactor (1) as well the aerosol is conveyed along a curved flow path through the non-linear USP throat (2) to the actual sample collector (5).

In accordance with human anatomy, the aerosol flow through the entry opening is conveyed into a first section (2a) of the USP throat (2) and then into a second section (2b) which is connected to the first section (2a) and arranged substantially perpendicular thereto.

The particles of the aerosol are subjected to radially outwardly directed centrifugal forces on account of the non-linear direction of flow and the resulting curved flow path. If the mass of the aerosol particles exceeds a certain size, these particles can no longer follow the deflected flow but are deposited on the walls of the USP throat (2).

FIG. 1 shows the flight path (12) of a particle which cannot follow the direction of flow and hits or is deposited on the inner wall of the second section (2b) of the USP throat (2).

This is in principle the first stage of the Andersen cascade impactor which simulates the deflection of the aerosol breathed in by the patient in the pharyngeal cavity and the resulting deposition of pharmaceutical formulation in the pharyngeal cavity.

The USP throat (2) is connected to the actual sample collector (5) via a connecting member (4), which is also standardised (loc. cit., page 123). The aerosol flow expands in the connecting member (4) and is guided towards the first stage or cascade ($6_1$) of the cascade impactor (1).

The cascade impactor (1) is a substantially cylindrical container of modular construction through which the aerosol fed in travels from top to bottom, passing through a number of stages, the so-called cascades, while the aerosol particles contained in the carrier medium are deposited in a sequence from coarse to fine or from heavy to light.

Each stage or cascade ($6_1$, $6_2$, $6_3$, $6_4$, $6_5$, $6_6$, $6_7$, $6_8$, $6_9$) comprises a plural impactor nozzles ($7_1$, $7_2$, $7_3$, $7_4$, $7_5$, $7_6$, $7_8$). An impactor nozzle (7) of this kind is shown diagrammatically in side view and in section in FIG. 3.

The aerosol which acts on the nozzle (7) is deliberately accelerated in the inlet aperture (8) of the nozzle (7) by a defined constriction of the cross section of the nozzle entrance and then deflected by means of an impactor plate (11). As in the deflection of flow in the USP throat (2), here too the curved path of movement and the centrifugal forces acting on the particles as a result cause particles of a certain mass to be deposited.

FIG. 3 shows the flow lines ($10_1$, $10_2$) of the aerosol flow, which the lighter particles essentially follow without colliding with the impactor plate (11). FIG. 3 also shows the flight path (12) of a particle striking the impactor plate (11) because of its excessively great mass.

The nozzle (7) acts to some extent as a filter for filtering out particles exceeding a given mass from the aerosol flow and depositing them on the impactor plate (11). Because of the fact that it is a standardised apparatus and a standardised process, accurate information is available as to the conditions in the region of the nozzle. For each cascade the precise mass $m_{ab}$ of the particles deposited on the impactor plate (11) here is known.

After passing through the first stage or cascade ($6_1$) and after the first depositing of heavy particles, the aerosol passes through eight more cascades ($6_2$ to $6_9$) as shown in FIG. 1, while the geometry of the impactor nozzles (7) varies or becomes finer from stage to stage and allows finer and finer, i.e. lighter, particles to be filtered out.

The aerosol particles deposited in a certain stage thus have a specific mass which is within a very narrow window bounded by an upper and lower limit.

As the last stage (not shown in FIG. 1) a filter may be provided which collects all the particles that have not previously been deposited and thus, together with the impactor plates (11), makes it possible to determine the absolute total mass of the pharmaceutical formulation fed into the impactor.

After the aerosol has passed through the impactor, the impactor plates (11) of each cascade are removed and subjected to extensive analysis. The main priority is to determine the particle size distribution. Theoretically, first of all the total mass of pharmaceutical formulation impacted or deposited on each impactor plate could be determined. By knowing the mass $m_{ab}$ of the particles deposited in each stage the number of particles deposited in each cascade can be calculated.

However, this process of aerosol analysis is time consuming and therefore not suitable for routine measurements with large batch numbers. The analysis of the different mass fractions on the impaction stages is very labour intensive. In addition, it has been found that the measurements thus obtained are not reproducible within narrow limits. Tests have shown that some of the pharmaceutical formulation evaporates during the measuring process.

Because of its unsaturated state the carrier medium can absorb additional liquid, and therefore liquid may be, and generally is, given off from the particles to the carrier medium by evaporation.

The evaporation of the particle droplets leads to a change in the particle mass of each individual particle and hence to a reduction in the particle diameter and consequently to a measurement which is falsified by evaporation.

The fact that the effects of evaporation may be significant is demonstrated in FIG. 4, which shows the lifespan of a drop of water depending on the initial droplet diameter for various relative humidities (0%, 50%, 100%) at 20° C. (William C. Hinds "*Aerosol Technology—Properties, Behavior, and Measurement of airborne Particles*", page 270, ISBN 0-471-08726-2).

Small particles have a short lifespan and may evaporate during measurement, so that they are no longer taken into consideration within the scope of the particle size distribution.

For the reasons stated it is not sufficient just to determine the total mass of the pharmaceutical formulation deposited on each impactor plate. Moreover, the pharmaceutical formulation of each impactor plate has to be subjected to analysis to determine the concentrations of the contents. Partial evaporation of the solvent or suspension agent causes concentration of the pharmaceutical substance and the other ingredients of the aerosol droplet.

On the basis of the degree of concentration of the pharmaceutical substance conclusions are drawn as to the fraction of the particle which is evaporated. Taking this evaporated fraction into consideration acts as a corrective when determining the particle size distribution and leads to a different total mass for the pharmaceutical formulation deposited on each impactor plate.

The pharmaceutical formulation deposited on the impactor plates (11) may, for example, be analysed for its composition by the HPLC method.

Further tests have shown that in spite of taking account of the evaporation as described above, the results still vary from one measurement to the next and it is desirable to increase the reproducibility still further. Other tests have shown that simply allowing for the mass of the evaporated fraction of the aerosol particles is not enough.

If a liquid pharmaceutical formulation contains acids or bases to adjust the pH, the evaporation that occurs during measurement leads to a raising or lowering of the pH. Consequently, in pH-sensitive active substances, decompositions occur, with the result that the analysis of the concentration of the active substance in the fractions deposited no longer corresponds to the concentration which was actually present in the original aerosol droplet. This procedure thus comes up against its limitations and can only be used to a limited extent as a corrective for the evaporation effect. A pharmaceutical solution or suspension might, for example, contain an acid X as excipient, in addition to the pharmaceutical substance A and water as the solvent. If some of the solvent water is evaporated, the pH is lowered and the particle becomes increasingly acidic, triggering breakdown of the pharmaceutical substance. The same is true if the pharmaceutical formulation contains a base.

As noted above, the analysis, i.e. the evaluation of the measurements made with the cascade impactor, is extraordinarily time-consuming and labour-intensive. The entire apparatus is taken to pieces in order to gain access to the multiplicity of impactor plates (11). Each impactor plate is weighed and analysed. Thus, as a rule, only a few measurements can be done per day and there is a considerable time span between the actual measuring and the results of the measurements becoming available.

Another process for determining the particle size distribution of an aerosol, which is far less time-consuming and labour-intensive than the impactor method, is the so-called laser diffraction method. Unlike the impactor method the laser diffraction method does not require any complex analysis and therefore makes it possible to work considerably faster and to obtain the results of the measurements much more quickly.

DIN-ISO 13320-1 (First Edition 1999-11-01) describes laser diffraction processes. In them, parallel light is transmitted perpendicular to an aerosol flow using a laser. The particles contained in the aerosol flow obstruct the laser beams, with the result that the light beams are diffracted on the particles. The scattered light emerging at the opposite side of the incident laser beam, which is generated by the diffraction of the laser beams on the particles, produces a circular interference pattern with concentric rings and is fed to a detector, usually a semiconductor detector. The usual methods of evaluating this interference pattern are Mie scattering and the Fraunhofer method.

Whereas the aerosol flow to be investigated is generally fed continuously to the cascade impactor through a USP throat, the particle size distribution of an aerosol is determined by the laser diffraction method according to the prior art on the free-flowing aerosol, i.e. usually on a one-off, conical, inhomogeneous and therefore non-reproducible metered stream.

However, a disadvantage of the laser diffraction method, as with the impactor method, is the fact that some of the aerosol particles are evaporated and thus the measurements are falsified. Although measurement of the aerosol by the laser diffraction method can be carried out much faster than the impactor method, in which the aerosol flow has to travel along a long flow path, the evaporation effect also plays a part in the laser diffraction method.

Precisely in the case of aerosols in which the particles are in the form of drops of liquid there is a danger of at least partial evaporation of the liquid aerosol particles, which means that the effects described are particularly significant in formulations in the form of solutions and suspensions.

The functional correlation shown in FIG. 4 and the need to take it into account were verified experimentally.

Experiments with the cascade impactor at various relative humidities have shown that measurements of the particle size distribution of an aerosol should most sensibly be carried out at high relative humidities, as the evaporation effect crucially influences the measurements if the humidity of the air is too low and finally high humidity levels also correspond to the actual conditions in the human oropharyngeal-cervical cavity. It should be taken into consideration that the processes described are to be used to determine the characteristics of deposition in the lungs and bronchial region, and for this reason every attempt should be made to simulate the conditions prevailing therein, i.e. pressure, temperature and humidity.

A third method of measuring aerosols is the scattered light method. Such a method is described by Dr. -Ing. H. Umhauer in VDI Berichte 232 (1975), pages 101ff. "*Ermittlung von Partikelgröβnverteilung in Aerosolströmungen hoher Konzentration mit Hilfe der Streulichtmethode*".

This method is suitable for measuring very fine particles with a detection limit which may be well within the submicroscopic range. The measuring process is set up as a counting process which detects the particle size and counts the individual particles so that it is possible to make pronouncements as to both the quality and quantity of the particles.

A disadvantage of the scattered light method is that a small measuring volume has to be defined, e.g. with sides 100 μm long, because only one particle may ever stop in the measuring volume if clear scattered signals are to be obtained. The apparatus and the calibration thereof are correspondingly complex. In practice the scattered light method has proved to be inferior to the laser diffraction method as its results are less reliable.

Moreover, the scattered light method, like the laser diffraction method, suffers from the evaporation effect with the associated disadvantages.

As in the conventional laser diffraction process, the scattered light method is also carried out on a free flow of aerosol.

To sum up, it can be said of the prior art that the cascade impactor is highly time-consuming and costly because of its complicated analysis, whereas the scattered light method and also the laser diffraction process, while offering comparatively fast processes, suffer from the evaporation effect, like the cascade impactor.

SUMMARY

The present invention provides a process to determine the particle size distribution of an aerosol, especially an aerosol of a pharmaceutical formulation.

In addition, the present invention provides a process for determining the particle size distribution of an aerosol which counteracts the previously noted disadvantages of certain techniques, and which minimizes the influence of the evaporation of the aerosol particles and increases the reproducibility of the measurements. Corresponding apparatuses are also provided in accordance with the invention that perform such processes.

In an embodiment of the invention, a method for measuring the particle size distribution of a pharmaceutical aerosol by the use of laser diffraction, where the method comprises generating an aerosol using an inhaler and spraying the aerosol into pre conditioned air with a relative humidity of at least 80%, and analyzing the sprayed aerosol using laser diffraction to determine an aerosol particle size distribution that is embedded into the pre-conditioned air.

For aqueous formulations, reproducible particle size distributions and strict correlation between the Andersen Cascade Impactor (ACI) and laser diffraction (LD) method can be obtained at ambient temperature and high humidity (RH>80%, preferably >85%, most preferably >90%). Air conditioning is preferable to avoid evaporation not only for ACI but also for LD. The LD results are quite stable against flow rate variations. The induction port should be used also for LD since it gives improved robustness of the method, closer conformance to existing ACI-methods, and facilitates method validation by coupling ACI and LD. The LD is a convenient substitute for the ACI if routine measurements are considered.

The above and still further features and advantages of the present invention will become apparent upon consideration of the following detailed description of specific embodiments thereof, particularly when taken in conjunction with the accompanying drawings.

BRIEF DESCRIPTION OF THE DRAWINGS

FIG. 2a to 2d show an USP throat with standardised geometric measurements.

FIGS. 6a to 6b show side views of an angled measuring cell.

FIG. 7 shows an embodiment of an apparatus for measuring the particle size distribution of an aerosol according to the present invention.

FIG. 8 shows a further exemplary embodiment of the set-up of a laser diffraction instrument, where the aerosol particles inside the illuminated region contribute to the diffraction pattern.

FIGS. 10a and 10b show exemplary embodiments of the modified USP throat, where FIG. 10a shows windows before the bend and FIG. 10b shows windows behind the bend (the inlet orifice for the laser beam is not visible).

DETAILED DESCRIPTION

Figure 1:
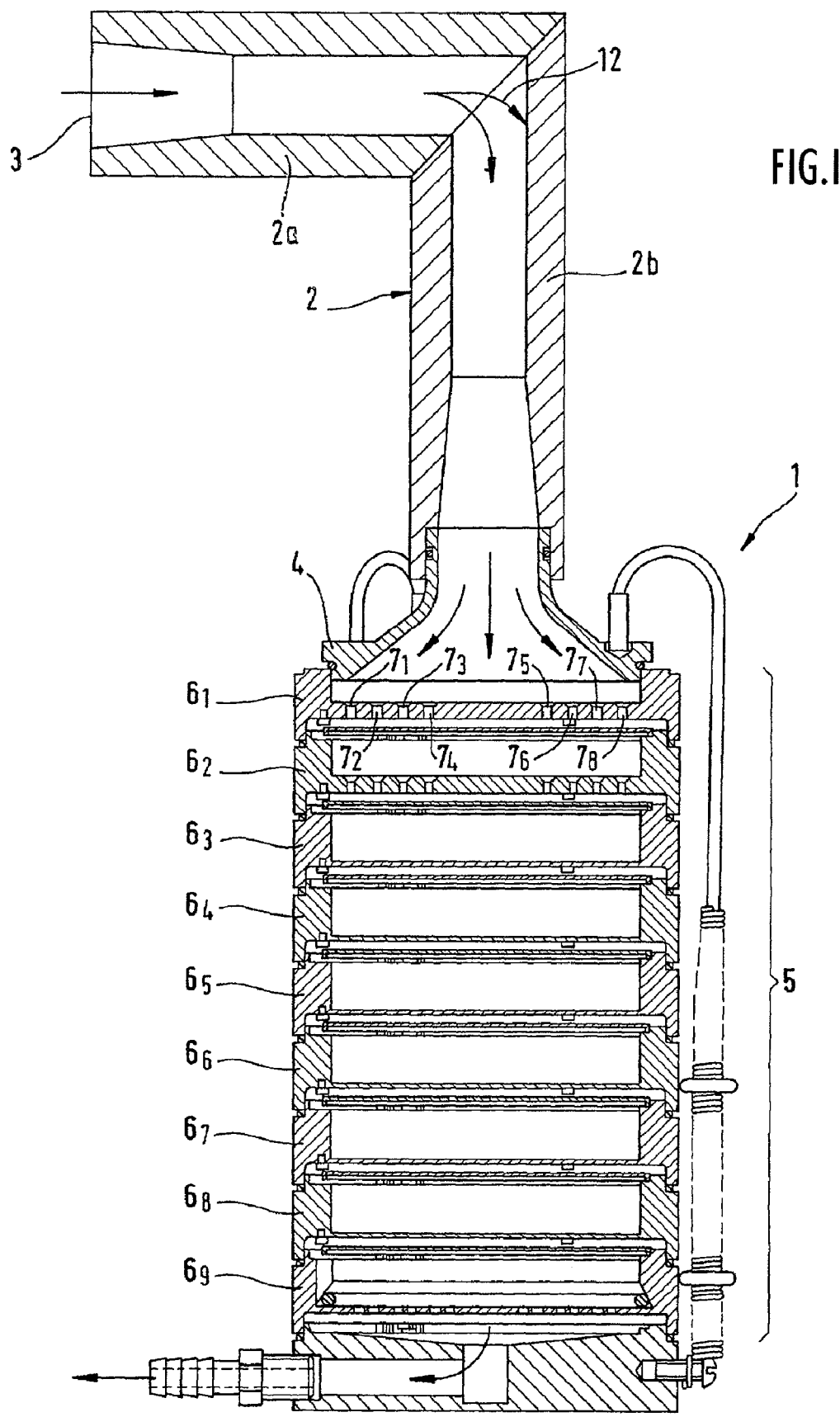
FIG. 1 is a side view of an Anderson impactor with an USP throat.
Figure 3:
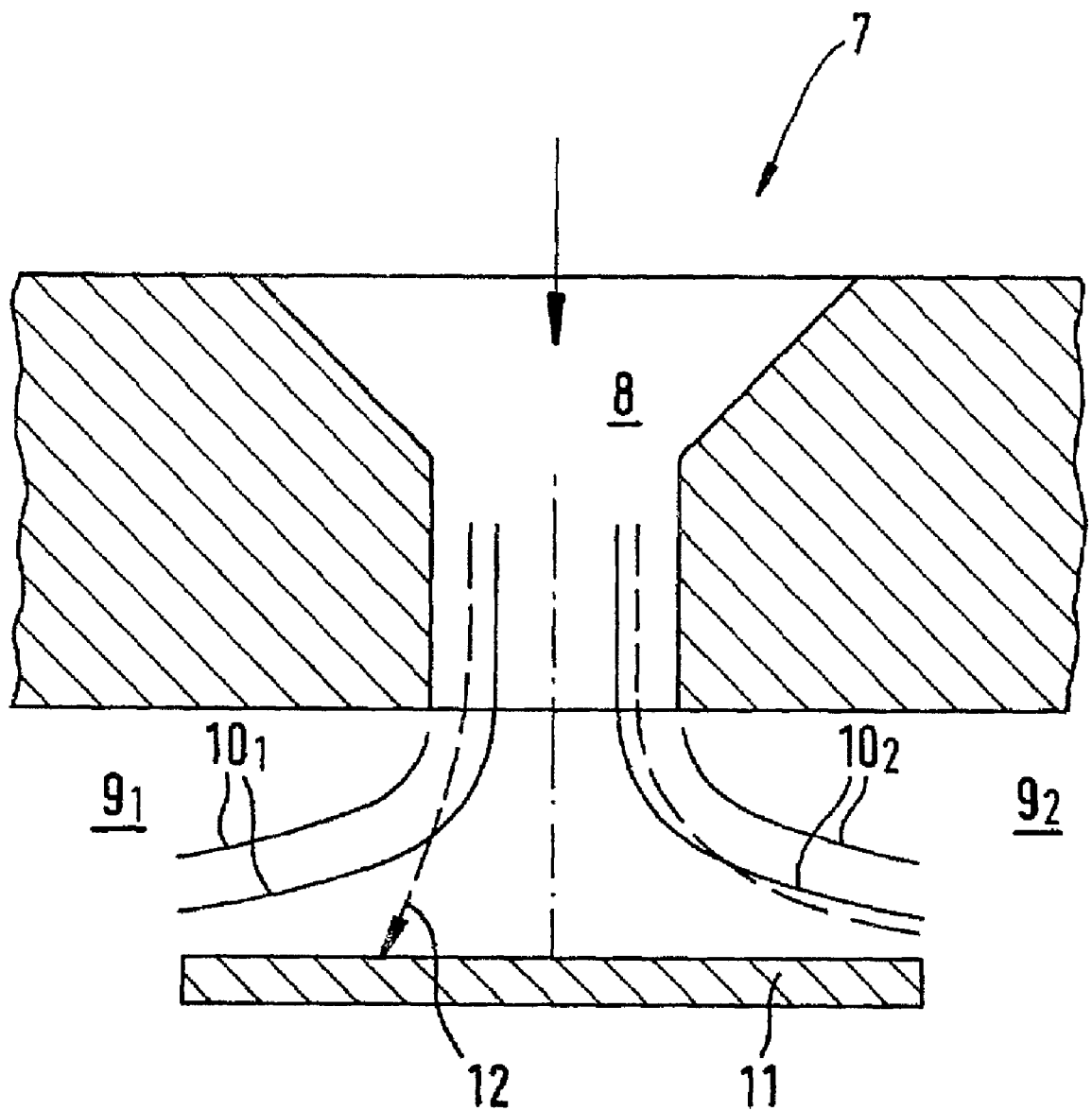
FIG. 3 shows an impactor nozzle.
Figure 4:
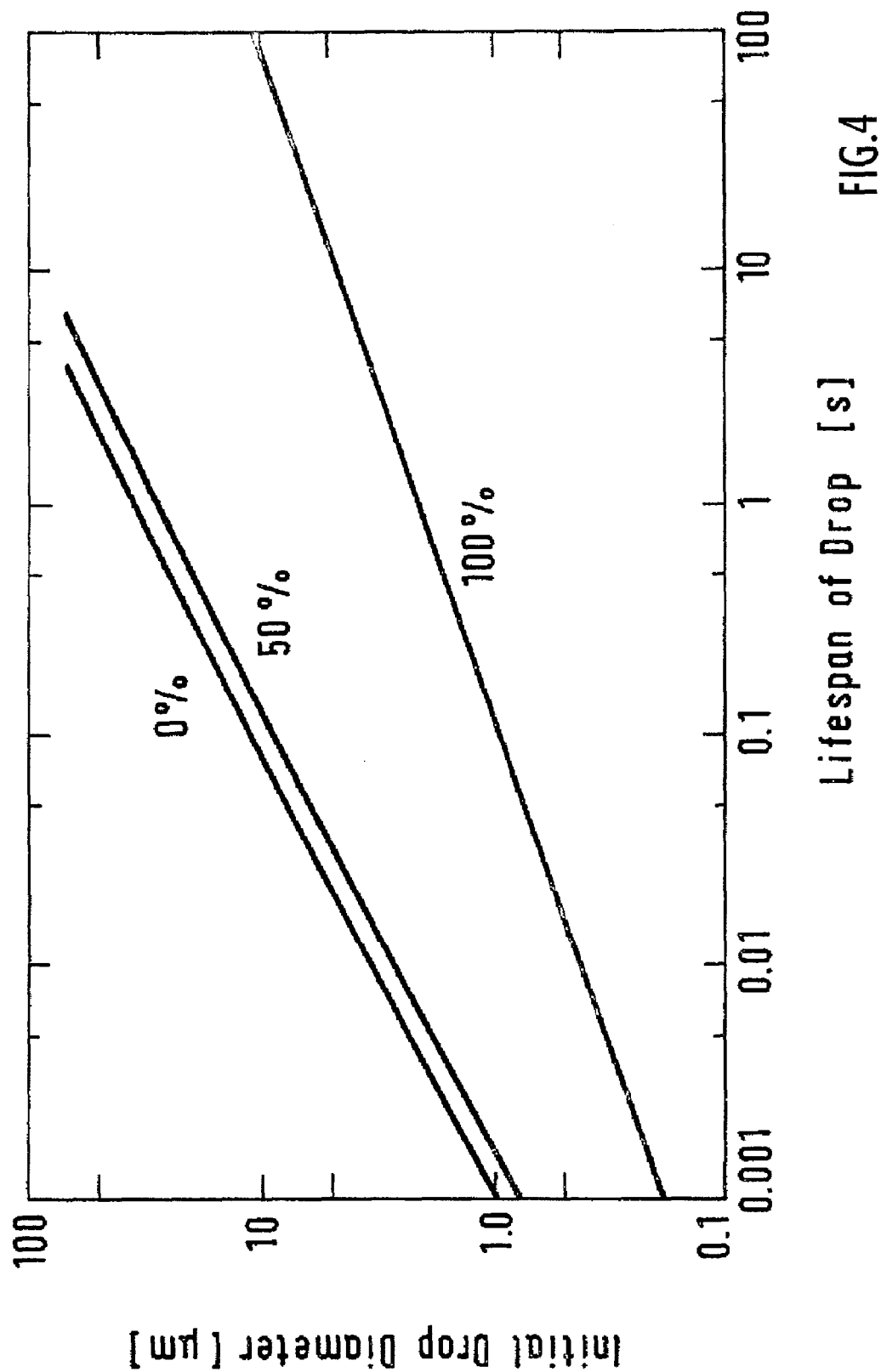
FIG. 4 is a chart showing dependency of droplet size on lifespan of droplet for three (3) different degrees of saturation with water.

Using an exemplary process of the invention, the carrier medium into which the aerosol is introduced is enriched with a conditioning agent according to a given degree of saturation. This measure counteracts any evaporation of the particles of a formulation in the form of a solution or suspension and all the other disadvantages connected with evaporation, particularly in substances which are sensitive to changes in pH.

In addition, the enrichment of the carrier medium with a conditioning agent mimics the actual conditions—particularly the high level of humidity—in the human oropharyngeal-cervical cavity, thereby creating measuring conditions which are as realistic as possible. Additionally the temperature and pressure can be adjusted as required.

The conditioning agent thus has two functions, while the establishment of a relative humidity, for basically all pharmaceutical formulations, which corresponds to the actual conditions ensures that the particle size distribution determined for the aerosol is as realistic as possible, thereby increasing the reliability of the measurement for evaluating the deposition characteristics in the lungs and bronchial region.

In the case of solution or suspension formulations the degree of saturation of the carrier medium is preferably more than 80%, more preferably more than 90%, most preferably more than 95%. Ideally it is 100%.

The carrier medium conditioned in this way is mixed with the pharmaceutical formulation under investigation in accordance with the process according to the invention to produce a conditioned aerosol. Atomisers or nebulisers as described in the introduction to the specification may be used for this purpose in the case of pharmaceutical solutions, for example.

Advantageously, once again an attempt is made to simulate reality as accurately as possible, for which reason the atomiser is preferably arranged in a mixing chamber in which the aerosol produced by the atomiser is mixed with the carrier material (air or some other gas) in order to direct the mixture in a defined flow from there through the measuring device. One advantage of the aerosol being guided in this way is that this approximates very closely to the conditions that prevail when an aerosol is being breathed in by a patient.

On the other hand, the carrier flow avoids any impact on the window of the measuring cell(s) in the case of liquid aerosols, which is an advantage particularly in the laser diffraction method. To produce this effect it is not necessary for the carrier material to be conditioned, i.e. saturated with water.

The carrier material may, for example, flow through slots in the mouthpiece of the inhaler into the interior of the mouthpiece, where it is mixed with the cloud of aerosol produced by the inhaler and introduced therein.

The conditioned aerosol thus generated is then fed into at least one measuring cell and measured in order to determine the particle size distribution of the aerosol.

In an advantageous process, the measurement of the conditioned aerosol is carried out by the laser diffraction method. The laser diffraction method, as further described below in relation to other embodiments of the invention, is a fast method which gives rapid access to the measurements.

In another advantageous process, the measurement of the conditioned aerosol is carried out by the scattered light method. The scattered light method gives not only a qualitative result—the particle size—but also a quantitative result, as the particles are not only measured for their size but are also counted.

In an advantageous process the measurement of the conditioned aerosol is carried out by the impactor method. As the impactor method is the one which is most widespread—inter alia because it is recommended and accurately described in the pharmacopoeias—and has been used for a great many measurements, this process offers a large fund of comparative measurements. Thus, when new pharmaceutical formulations and/or new metering devices, particularly atomisers, are being tested it may be sensible to compare them with conventional pharmaceutical formulations or metering devices.

In an advantageous process the measurement of the conditioned aerosol is carried out by the laser diffraction process and the scattered light method. Using the two methods together combines the advantages of both methods, namely the accuracy of the laser diffraction process in qualitative terms with the scattered light method as a particle counting method and hence the possibility of making quantitative pronouncements.

Favorable methods are characterised in that the conditioned aerosol is also measured by the impactor method. In this alternative embodiment of the process the impactor method additionally used serves primarily to verify the measurements obtained by the process according to the invention. Tests have shown that the measurements obtained with the two methods largely agree.

In the process according to the invention, the particle size distribution of the aerosol may optionally be carried out either by the laser diffraction method or by the scattered light method or using both methods, i.e. the laser diffraction method and the scattered light method, while if both methods are used they are carried out together in one measuring cell or a separate measuring cell is provided for each process, so that both processes have their own measuring cell to suit their own particular requirements.

Experimental tests have shown that the process according to the invention, particularly the laser diffraction method, in a conditioned aerosol flow agrees closely with the measurements obtained using the Andersen cascade impactor.

In an advantageous embodiment of the process in which a solution formulation, i.e. a solution of pharmaceutical substance, is used, the solvent in which the pharmaceutical substance is dissolved is used as the conditioning agent. In order to prevent evaporation of the solvent contained in the aerosol particles, the solvent whose evaporation is to be inhibited is advantageously added to the carrier medium as a conditioning agent. The addition of the solvent as a conditioning agent lowers the vapour pressure of the solvent in the carrier medium, thereby making it more difficult for the liquid aerosol particles to evaporate, or reducing the amount of evaporation.

In preferred variants of the process in which a suspension formulation, i.e. a suspension of pharmaceutical substance, is used, the suspension agent containing the pharmaceutical substance in the form of suspended particles is used as the conditioning agent. The reasons for this are similar to those mentioned for the solution formulation. In order to prevent or reduce the evaporation of the suspension agent contained in the aerosol particles, the suspension agent is preferably added as the conditioning agent to the carrier medium, as a result of which the vapour pressure of the suspension agent in the carrier medium is lowered and hence the tendency to evaporation is counteracted.

According to favorable variants, if a propellant-free dissolved or suspended formulation is used, the solvent or suspension agent is used as the conditioning agent. Water, water/alcohol mixtures or alcohol are preferred. The preferred alcohol is ethanol. Water is most preferred.

Because the powder formulation, unlike the solution and suspension formulations, does not have any solvent or suspension agent, water is preferably added as conditioning agent to the carrier medium.

This comes very close to the actual conditions because the moist air breathed in by the user, which acts as a carrier medium for the powder, can be satisfactorily simulated or reproduced experimentally by air saturated with water as conditioning agent.

In contrast to the other two pharmaceutical formulations, in a powder formulation a preferred process is one wherein the carrier medium does not exceed a saturation level of 75%, as the pharmaceutical substance present in the form of a fine powder tends to form larger particles and particularly to cake together at higher saturation levels.

Also advantageous are variants of the process in which air is used as the carrier medium. One reason for this is that again the use of air as a carrier medium corresponds to the actual conditions and thus provides a good simulation in the experiment.

In advantageous processes a USP throat, through which the aerosol flow passes, is used within the scope of the measurement. This simulates the flow through the oropharyngeal-cervical cavity.

In advantageous processes the measurement of the particle size distribution of the aerosol by the laser diffraction process and/or the scattered light method is carried out in at least one measuring cell which is separated from the surrounding atmosphere. To maintain the conditioning and stabilise the conditioned aerosol, i.e. to separate it from the surrounding atmosphere, a suitable prepared measuring cell is advisable.

Preferred embodiments of the process are those wherein the measurement of the particle size distribution of the aerosol by the laser diffraction method and/or the scattered light method is carried out in at least one measuring cell integrated in the USP throat. The USP throat is a test device recognised by the FDA (Food and Drug Agency).

The or each measuring cell may be arranged both in the first section of the USP throat and also in the second section of the USP throat. Moreover, when two measuring cells are provided, there is the possibility of arranging one measuring cell in the first section and the second measuring cell in the second section of the USP throat, while once again it is also possible to arrange both measuring cells in the first or second section of the USP throat.

This or each measuring cell is in fact shown in FIGS. 2a to 2d and integrated in the USP throat described in detail hereinbefore.

It is thus possible to carry out the laser diffraction process and/or the scattered light method on a defined, well known aerosol flow. The measurement of the particle size distribution on a free, inhomogeneous and non-reproducible aerosol cloud, which is regarded as disadvantageous, is thus replaced by a defined process using standardised equipment.

Surprisingly, tests have shown that by suitably modifying the USP throat in order to integrate at least one measuring cell the advantages of the laser diffraction process and/or the scattered light method can be combined with the advantages of the impactor method using the USP throat, while the experts will be astounded to discover that the modification, i.e. the structural alteration of the USP throat, has no effect on the measurements obtained for the particle size distribution.

Figure 5:
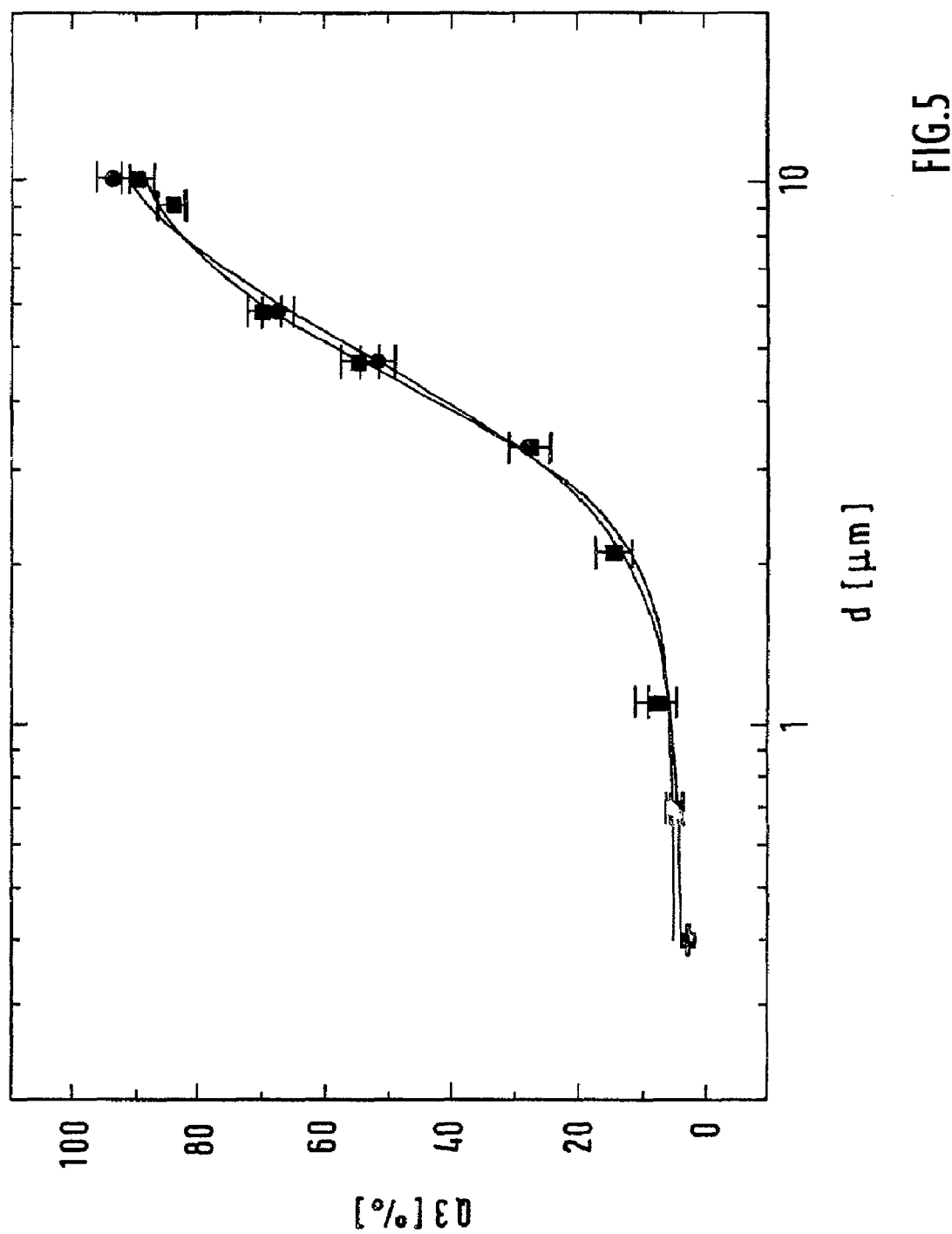
FIG. 5 is a chart comparing properties of a conventional USP throat with one modified with an angled measuring cell according to the present invention.

This has been verified in numerous experiments, in which a conventional cascade impactor was fitted with the modified USP throat and comparative measurements were taken which were compared with the measurements using the conventional USP throat. The results of the comparative measurements are shown in FIG. 5, in which the distribution sum $Q_3$ is shown as a function of the particle diameter. The measurements marked with a small square represent the results of a cascade impactor fitted with an original throat, whereas the measurements marked with a small circle are the measurements obtained with a cascade impactor fitted with the modified USP throat according to the invention. Very good correspondence is obtained, so that it may reasonably be concluded that the modification of the USP throat does not substantially alter the data obtained with the original throat.

Thus, the process according to the invention which provides for the arrangement of at least one measuring cell in the USP throat is suitable for replacing the conventional process using cascade impactors, which do not produce rapid measurements on account of the complicated analysis required.

An advantage of this variant of the process is that the USP throat is an exactly standardised component which simulates the oropharyngeal-cervical cavity in humans, and ensures a precisely defined flow of aerosol.

According to favorable embodiments of the process, the metered aerosol is fed into a separator in order to separate off the particles. This is done in order to determine the total absolute particle mass of the particles or pharmaceutical formulation delivered with the aerosol. A filter may be used as the separator.

This is particularly favorable in conjunction with the variant of the process according to the invention in which the laser diffraction process is not carried out together with the scattered light method but is used on its own. In this case, in fact, there is a need for an apparatus which will provide quantitative information on the particle mass delivered.

Whereas the scattered light method provides both qualitative and quantitative results, i.e. gives information on both the size distribution and on the particle masses, the laser diffraction process can only provide information as to the size distribution and not on the quantity of aerosol particles.

Processes wherein a laser is used as the light source for the laser diffraction process or the scattered light method are favorable. An advantage of the use of a laser is that it emits parallel light.

The problem of the equipment required is solved by an apparatus including:
  a conditioning device for saturating a carrier medium with a conditioning agent according to a given saturation level,
  a metering device for metering and preparing a pharmaceutical formulation,
  a mixing chamber for mixing the prepared, conditioned carrier medium and the prepared pharmaceutical formulation to produce a conditioned aerosol, and
  at least one measuring cell into which the conditioned aerosol is introduced in order to carry out a measurement of the particle size distribution of the aerosol.

In advantageous embodiments of the apparatus, the or each measuring cell for carrying out the impactor method is an impactor, preferably an Anderson cascade impactor.

In advantageous embodiments of the apparatus, the or each measuring cell for carrying out the laser diffraction process has an least one entry window for the entry of a light beam from a light source and at least one exit window for the exit of the scattered light from the light beam, while preferably the or each entry window is arranged at a tilted angle to the incident light beams from the light source and preferably the or each exit window is arranged at a tilted angle to the incident light beams. Reflections are avoided by the fact that the light beam does not strike perpendicularly on the entry or exit window.

According to advantageous embodiments of the apparatus, each entry window (e.g., one or more) and each exit window (e.g., one or more) are arranged to be tilted at identical—but opposite—angles relative to the incident light beams. As a result of the two windows being tilted opposite ways and at the same angle the offset of the incident and emergent light beams is cancelled out again because of the tilt.

In favorable embodiments of the invention, each entry window and/or the or each exit window are constructed to be removable. This makes it possible to clean not only the measuring cell but also the window itself after the measurement has been done and to investigate any deposit of aerosol particles in the measuring cell and on the windows.

According to advantageous embodiments of the invention, each entry window and each exit window are thin in construction, particularly less than 2 mm thick. An advantage of this embodiment is that the incident or emergent light beam which preferably falls diagonally on the tilted windows and which is diffracted as it enters the glass from the ambient atmosphere undergoes only a small displacement of the beam if the windows are thin.

According to advantageous embodiments of the invention, each measuring cell (e.g., one or more) for carrying out the scattered light method has at least one entry window for the entry of a light beam from a light source and at least one exit window for the exit of the scattered light from the light beam, the two windows preferably being arranged substantially at right angles to each other.

The problem of the equipment according to an embodiment of the invention is solved by an apparatus, particularly an apparatus for carrying out the second process according to the invention, which specifically has the following components:
- a metering device for metering and preparing a pharmaceutical formulation,
- a mixing chamber for mixing a prepared carrier medium and the prepared pharmaceutical formulation to produce an aerosol, and
- at least one measuring cell into which the aerosol is introduced in order to measure the particle size distribution of the aerosol by the laser diffraction process and/or the scattered light method, the or each measuring cell being integrated in the USP throat and forming, together with this throat, an angled measuring cell.

The invention also discloses an angled measuring cell, particularly as a component or replacement part for an apparatus for carrying out the process according to the invention, which comprises the USP throat and at least one measuring cell integrated in the USP throat.

According to advantageous embodiments of the measuring cell, each measuring cell for carrying out the laser diffraction process has at least one entry window for the entry of a light beam from a light source and at least one exit window for the exit of the scattered light from the light beam.

According to favorable embodiments of the angled measuring cell, each entry window is arranged at a tilted angle to the incident light beams from the light source and preferably the or each exit window is arranged at a tilted angle to the incident light beams, while each entry window and each exit window are arranged to be tilted at identical—but opposite—angles relative to the incident light beams.

In favorable embodiments of the angle measuring cell, each entry window and/or each exit window are constructed to be removable. According to advantageous embodiments of the angled measuring cell, each entry window and each exit window are thin in construction, particularly less than 2 mm thick, each entry window and each exit window being arranged opposite each other. According to advantageous embodiments of the angled measuring cell, the or each entry window and the or each exit window of the or each measuring cell for carrying out the scattered light method are arranged substantially at right angles to each other.

One embodiment of the present invention is described with reference to an embodiment, by way of example, illustrated in FIGS. 6*a*, 6*b* and 7. Specifically, as noted previously, FIG. 1 shows an Andersen cascade impactor with the USP throat in side view, partly in section, while FIGS. 2*a* to 2*d* show the USP throat with its standardised geometric measurements, FIG. 3 shows an impactor nozzle shown diagrammatically and in section in side view, FIG. 4 shows a diagram relating to the dependency of the droplet size on the life of the droplet, for three different degrees of saturation with water, FIG. 5 shows a diagram comparing the properties of a conventional USP throat with those of the angled measuring cell, FIGS. 6*a* to 6*b* show an embodiment of an angled measuring cell in different side views, partly in section, and FIG. 7: shows an embodiment of the apparatus for measuring the particle size distribution of the aerosol.

In FIGS. 1, 2*a*-2*d*, 3, 6*a*-6*b* and 7, the following numbers are used for the following parts:

1 Andersen cascade impactor
2 throat
2*a* first section
2*b* second section
3 entry opening
4 connecting member
5 sample collector
$\mathbf{6}_1$ cascade
$\mathbf{6}_2$ cascade
$\mathbf{6}_3$ cascade
$\mathbf{6}_4$ cascade
$\mathbf{6}_5$ cascade
$\mathbf{6}_6$ cascade
$\mathbf{6}_7$ cascade
$\mathbf{6}_8$ cascade
$\mathbf{6}_9$ cascade
$\mathbf{7}_1$ impactor nozzles
$\mathbf{7}_2$ impactor nozzles
$\mathbf{7}_3$ impactor nozzles
$\mathbf{7}_4$ impactor nozzles
$\mathbf{7}_5$ impactor nozzles
$\mathbf{7}_6$ impactor nozzles
$\mathbf{7}_7$ impactor nozzles
$\mathbf{7}_8$ impactor nozzles
8 entry opening
$\mathbf{9}_1$ exit opening
$\mathbf{9}_2$ exit opening
$\mathbf{10}_1$ flow lines
$\mathbf{10}_2$ flow lines
11 impactor plate
12 flight path of a striking particle
20 angled measuring cell
21 entry window
22 exit window
23 measuring cell
24 conditioning device 25 mixing chamber
26 metering device, nebuliser
27 laser
28 lens
29 semiconductor detector FIG. 6a shows a first embodiment of an angled measuring cell 20 which comprises a USP throat 2 and a measuring cell 23 for carrying out the laser diffraction process. The measuring cell is arranged in the first section 2a of the USP throat, so that the current of aerosol is measured even before the first particle fraction has been deposited in the angled section at the transition from the first section 2a to the second section 2b.

The measuring cell 23, shown in section, has an entry window 21 and an exit window 22. The two windows 21, 22 are constructed to be removable so that after the measurement has been done the measuring cell 23 can be cleaned and examined. Both the entry window 21 and the exit window 22 are tilted slightly, relative to the incident light beam, thus preventing reflection of the incident light beam. The two windows 21, 22 are tilted at the same angle, but opposite one another, in order to compensate for the offset of the beam of the incident laser light as a result of the tilt.

It is clearly apparent that the entry window 21 is relatively small compared with the exit window 22. The reason for this is that the incident light coming through the entry window 21 is an undisturbed beam of light which is propagated in linear manner, whereas the light leaving through the exit window 22 is the scattered light from the incident light beam diffracted on the aerosol particles, for which reason the exit window 22 should also be constructed so that scattered light from a large enough angular area can be accommodated, i.e. is able to leave the measuring cell 23 and be picked up by a detector.

FIG. 6b shows the angled measuring cell 20 shown in FIG. 6a, in a view turned through 90° relative to the position shown in FIG. 6a, partly in section.

It clearly shows the USP throat 2 consisting of the first section 2a and the second section 2b, and the measuring cell 23 integrated therein in the first section 2a. In this way the aerosol flow entering through the inlet opening 3 is measured before it is deflected through the angled section into the second section 2b. The Figure also shows the flight path of a particle striking the inner wall of the second section 2b which with the other particles arriving at this point forms the first deposited fraction of the aerosol flow. In accordance with an embodiment of the present invention, a laser diffraction (LD) method is provided. The set-up of a typical laser diffraction instrument is shown in FIG. 2.

A laser is used to generate a monochromatic, coherent, parallel beam that illuminates the dispersed particles after expansion by the beam processing unit. The measuring zone should be in the working distance of the lens used. The interaction of the incident light beam with intensity (I) and the ensemble of dispersed particles results in a scattering pattern with different light intensities at various angles. The total angular intensity distribution (I(θ), consisting of both direct and scattered light, is then focused by a lens system onto a multi-element detector. In this way, the continuous angular intensity distribution (I(θ)) is converted into a discrete spatial intensity distribution (I(r)) on a set of detector elements. By means of a computer the particle size distribution can be calculated which best approximates (I(r)).

In order to introduce and establish the laser diffraction method according to the invention as a tool that may replace the cascade impactor for routine measurements on pharmaceutical inhalers, the equivalence of both methods must be proven.

Using continuously operating nebulizers, Clark (Clark, A. R. 1995), laser diffraction is used for the evaluation of the aerosol clouds generated by medical nebulizers. International Journal of Pharmaceutics 115: 69-78), Kwong et. al. (Kwong, W. T. J., S. L. Ho, A. L. Coates. 2000. Comparison of nebulized particle size distribution with Malvern laser diffraction analyser versus Andersen cascade impactor and low-flow Marple personal cascade impactor. Journal of Aerosol Medicine 13: 303-314) and None et. al. (None, L. V., D. Grimbert, M. H. Bequemin, E. Boissinot, A. le Pape, E. Lemarié P. Diot. 2001. Validation of laser diffraction method as a substitute for cascade impaction in the European project for a nebulizer standard. Journal of Aerosol Medicine 14:107-114) established a good correspondence between the methods regarding the aerodynamic diameters and the geometrical standard deviations.

Ziegler and Wachtel (WO 03/012402 A1) described the first successful attempt to establish a correlation between laser diffraction and cascade impaction using aqueous aerosols generated by soft mist inhalers.

For the present invention, dedicated equipment is required as the soft mist inhalers generate a high particle density ($>10^6$ particles/cm$^3$) for a time span of 1.5 s or less. The measurements were performed simultaneously and evaporation was accounted for by a comparison between volatile liquid and non-volatile aerosols. The aqueous aerosols were generated by a soft mist inhaler which was operated with humidified air with a RH of preferably >90%. The measurements were performed at ambient temperature. For the simultaneous measurement of the PSD with LD and ACI the induction port (also denoted USP-throat) was modified without changing the characteristic impactor geometry.

FIG. 7 shows an embodiment of an apparatus for measuring the particle size distribution of an aerosol, shown diagrammatically.

The apparatus comprises a conditioning device 24 for saturating a carrier medium with a conditioning agent to a given degree of saturation. The carrier medium thus conditioned is fed into a mixing chamber 25 which contains a nebuliser to be examined, which atomises a solution of pharmaceutical substance stored therein. The nebuliser 26 acts as a metering device 26 for metering and preparing a pharmaceutical solution. The pharmaceutical solution prepared using the metering device is mixed with the conditioned carrier medium in the mixing chamber 25 to form a conditioned aerosol.

The aerosol conditioned in this way is introduced into a measuring cell 23.

This measuring cell 23 is arranged in a first section 2a of the USP throat 2 and together with the throat 2 forms an angled measuring cell 20, which is surrounded by a dotted line in FIG. 7.

The light emitted by the laser 27 falls through the entry window 21 into the interior of the measuring cell 23 and from there strikes the aerosol flow guided by the first section 2a of the USP throat 2. The incident laser light is diffracted on the particles of the aerosol, which constitutes an obstacle to the light. The scattered light which is generated by the diffraction of the incident laser light on the particles of the aerosol leaves the measuring cell 23 through the exit window 22, is then focussed through a lens 28 and fed into a semiconductor detector 29 for evaluation. After being measured in the measuring cell the aerosol flow is diverted into the second section 2b of the USP throat 2. After passing through the throat 2 or the angled measuring cell 20 the aerosol flow measured by the laser diffraction process can be fed into a particle separator in order to obtain quantitative information on the particle mass; the particle separator may take the form of a filter.

An additional measuring cell for obtaining a measurement by the scattered light method could be provided, in which case this measuring cell would be arranged both in the first section 2a and in the second section 2b of the USP throat 2. This would also make it possible to obtain quantitative information on the particle mass.

The apparatus shown in FIG. 7 could also have an Andersen cascade impactor adjacent to it, which could be used inter alia to verify the particle size distribution of the aerosol determined by the laser diffraction method.

Thus, the measurement of the particle size distribution of an aerosol is of crucial importance in the pharmaceutical industry. The prerequisite for this is a valid method, e.g. the cascade impactor method described in the pharmacopoeias. It requires measurement of the active substance concentration in order to determine the particle size distribution.

However, the above method and other methods as well rapidly lead to an increase or decrease in the pH, which may lead to decomposition of sensitive active substances. Consequently, the particle sizes can no longer be determined precisely, as it is usual to determine the concentration of active substance in order to obtain the particle size.

Surprisingly, it has been shown that by adjusting the relative humidity to 80 to 100%, preferably 90 to 100%, using the solvent on which the solution or suspension formulation is based, preferably water or a water/alcohol mixture (ethanol), the breakdown of the active substance during the measuring process can be totally prevented.

Another advantage of the process according to the invention is that the particle size can be determined irrespective of the nature of the aqueous formulation, i.e. different salt concentrations in the solution or suspension have no effect on the measurement of the particle size.

It has also advantageously been found that the measurement of the particles is not disrupted when water condenses out in the measuring apparatus, particularly the cascade impactor, during the measurement.

Compared with the standard measurement without conditioning the air with a solvent such as water the relative standard deviation can be improved from 10-15% to about 2% using the process according to the invention.

At a relative humidity of 100% the method shows a significantly lower scattering in the MMAD (mass median aerodynamic diameter) than the standard method without conditioning of the air with a solvent such as water.

For the process according to the invention, water saturated with moisture can be produced by passing compressed air through a water bath heated to above ambient temperature; the water temperature is preferably about 30 to 45° C.

The process can be used to measure the spray pattern of a propellant-free "soft mist inhaler", preferably known under the trademark Respimat®, disclosed for example in WO 97/12687. Preferred formulations are described in WO 97/01329 and WO 98/27959, to which reference is hereby expressly made.

In accordance with another embodiment of the invention, the Andersen Cascade Impactor (ACT) and the Laser Diffraction method (LD) can be correlated for aqueous drug formulations at ambient temperature. A comparison of the two particle size determination methods at different conditions (flow rate, relative humidity) was performed. Under well defined conditions, the Particle Size Distribution (PSD) is independent of the method of investigation, and the faster LD, which is subject of the present invention, can substitute the time consuming ACI at least for routine measurements.

The measurements were performed with three different drug formulations. The aerosol was generated by soft mist inhalers, such as the Respimat®-device as disclosed in WO97/12687 (as set forth in FIGS. 6a and 6b of this reference), and the droplet distributions were measured simultaneously using a laser diffraction analyser together with an 8-stage Andersen cascade impactor (such as the type described above and depicted in FIG. 1). In order to measure the scattered laser light intensity of the aerosol passing the induction port, according to the invention glass windows were fitted to the induction port. The evaporation effect of the aqueous aerosols on the PSD was investigated at ambient humidity and high humidity (RH>90%). The simultaneous determination of the droplet size distribution leads to a good correlation between the ACI and LD method, in particular if the measurements were performed at RH>90%. The humidity of the ambient air shows interesting influence on PSD. Best results were achieved if the air was almost saturated with humidity. The influence of the flow rate on LD was negligible, whereas for ACI, the expected flow rate dependence holds. The advantages of LD and the demonstrated compatibility to established EP/IUSP methods motivate the substitution of the ACI and the use of LD for routine measurements.

In the following description below the following abbreviations are used:
alpha: level of significance (alpha=0.05 in this report)
ACI: Andersen cascade impactor
c: concentration of the drug formulation
CF: cumulative undersize fraction
$D_{16}$: diameter at 16% cumulative fraction
$D_{50}$: diameter at 50% cumulative fraction
$D_{84}$: diameter at 84% cumulative fraction
FPF(<5.8 μm): Fine particle i.e. fraction of particles with diameters less than 5.8 micrometer
I(θ): Intensity of diffracted light as function of angle
θ (Greek theta)
I(r) spatial intensity distribution
lambda: laser wavelength
LD: Laser diffraction
micron: micrometer
PSD: Particle size distribution
RH: relative humidity
SD: Standard deviation
Sigma g (as well as written as Greek letter): geometric standard deviation
T: Boiler temperature of the Sinclair LaMer aerosol generator For the study, Respimat® soft mist inhalers were used to generate the aqueous aerosols. The investigated formulations contained different active drugs (active drug concentration c indicated) as well as excipients. They are called Formulation A (c=0.049 %), Formulation B (c=0.198%), and Formulation C (c=0.833%). By this choice, the concentration c of drugs ranged from c=0.049%, 0.198% to 0.833%. A single actuation of the inhaler resulted in a spray duration of 1.5 seconds.

The non-volatile aerosol was generated with a Sinclair-LaMer type aerosol generator MAG-2010 (PALAS® GmbH in D-76229 Karlsruhe, Germany). This aerosol was used for testing the reliability of the laser diffraction analyser. The generator is configured to generate adjustable particle diameters between approximately 0.3 micrometer and 6 micrometer with a geometric standard deviation sigma g less than 1.15 and a number concentration up to $10^6$ cm$^{-3}$. In the boiler, where the aerosol material is vaporised, the temperature controls the particle diameter. The corresponding aerosol material is DEHS (Di-2-Ethylhexyl-Sebacate).

Aerosol droplet distributions were measured using the Sympatec HELOS laser diffraction analyser (Sympatec GmbH, D-38678 Clausthal-Zellerfeld, Germany) at lambda=632.8 nm (He—Ne laser) together with an Andersen Mark II 8-stage cascade impactor operated at 28.3 L/min with the corresponding cut-off points 0.4, 0.7, 1.1, 2.1, 3.3, 4.7, 5.8 and 9.0 micrometer. As an experimental restriction, particles with diameters below 1 micrometer are hardly detectable with the LD configuration used for the presented measurements.

The analysis of the drug was performed in the case of Formulation C with an UV/VIS scanning spectrophotometer at the wavelength lambda=218 nm and sometimes additionally at the wavelength lambda=276 nm. The detection of the other two Formulations A and B was performed with standardised HPLC because of their lower drug concentrations.

For the control of the reliability of the generated data, the laser diffraction apparatus was tested with a reference reticle. The reference reticle consists of silicon particles of defined sizes deposited onto a glass slide. The size distribution of the reticle was measured with the laser diffraction apparatus used for the measurements and with a laser diffraction apparatus of the same type as a reference. The results were compared with the nominal values given for the reference reticle. The laser diffraction analyser was additionally tested with a monodisperse aerosol. The generation process of the test aerosol is based on the Sinclair-LaMer principle by condensation of the vaporised aerosol material at nuclei. The “heart” of the generator is the condensation nuclei source. The nuclei source was a pure sodium chloride solution, the aerosol material was DEHS (Di-2-Ethylhexyl-Sebacate). Three different monodisperse particle size distributions with $D_{50}$ values between 2 micrometer and 6 micrometer were generated and measured simultaneously with the laser diffraction analyser and the cascade impactor.

Evaporation Effects

Figure 9:
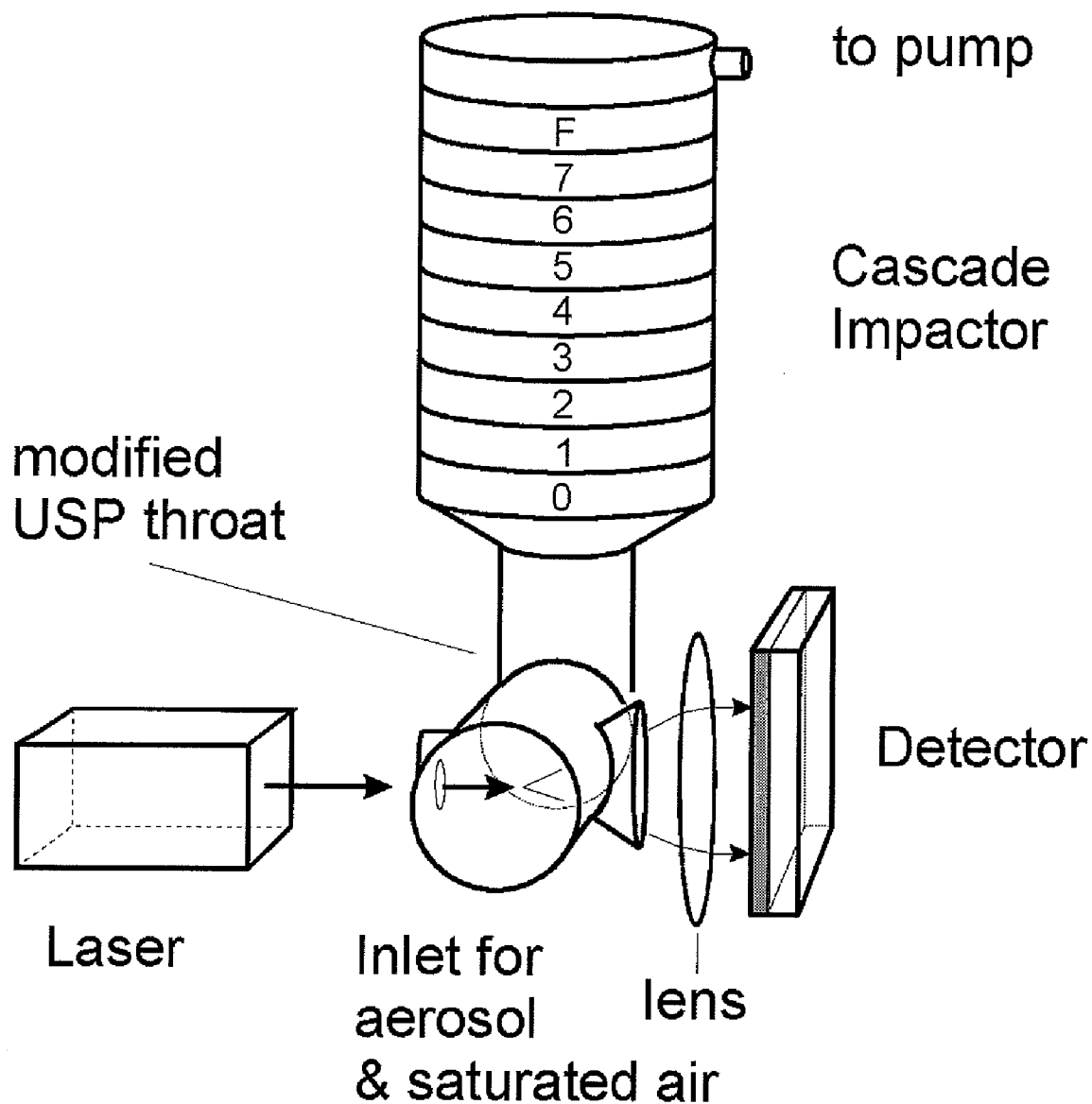
FIG. 9 shows a front side view of the experimental set-up for simultaneous particle size distribution measurements with the cascade impactor and laser diffraction that is similar to the embodiment of FIG. 7, where the distance from the center of the measurement cone to the lens is 4 cm.

In addition to measurements under ambient humidity (relative humidity RH about 30%-45%) the particle size distribution was investigated under water vapour saturated air (RH >90%) conditions to study the evaporation effect of the aqueous aerosols. The schematic experimental set-up is shown in FIG. 9 (which is similar to the embodiment described above and depicted in FIG. 7).

In order to measure the scattered laser light intensity of the aerosol passing the induction port, two holes were drilled in front of the bend of the port which were sealed with 0-rings and glass windows. A three dimensional side view of the modified USP throat is presented in FIG. 10*a*.

Some experiments were also performed with an induction port having the holes and glass windows behind the bend (as shown in FIG. 10*b*). This bend represents a first impaction stage for large particles and therefore these particles can be detected neither by the laser diffraction nor by the cascade impactor. From the point of view of quality control, the windows positioned before the bend are preferred, because in this position all droplets can be detected by the laser system.

Irrespective of the window position, it is possible with this set-up to measure the PSD with the cascade impactor and the laser diffraction method simultaneously. To ensure sufficient drug deposition on all the impactor plates to allow for UV spectrophotometric or HPLC analysis, 4 to 8 actuations per measurement were collected. For the laser diffraction data analysis the Mie-theory is used which is applicable for transparent spheres (Kerker, M. 1969. The scattering of light and other electromagnetic radiation. Academic Press, New York). For that purpose the refraction and absorption index of the droplets must be known. The refraction index of the aqueous aerosol particles was 1.33 and the absorption was 0.0. For the DEHS particles, the refraction index was 1.45 and the absorption was 0.0. The advantage of the Mie correction is that it takes into account the increased scattering of light from smaller droplets compared to the Fraunhofer theory (Merkus, H. G., J. C. M. Marijnissen, E. H. L. Jansma, B. Scarlett. 1994. Droplet size distribution measurements for medical nebulizers by the forward light scattering technique. Journal of Aerosol Science 25 Suppl. 1: S319-S320 and Corcoran, T. E., R. Hitron, W. Humphrey, N. Chigier. 2000. Optical measurement of nebulizer sprays: A quantitative comparison of diffraction phase doppler interferometry, and time of flight techniques. Journal of Aerosol Science 31: 35-50).

The PSD measured with laser diffraction was calculated automatically from the scattered light intensities striking the 31 detector elements. The Sympatec HELOS software used for the calculation was WINDOX version 3.3.

The basis for the calculation of the PSD measured with the cascade impactor was the total mass detected with the photometer or HPLC i.e. the total mass is the sum of all masses recovered on the different impaction stages and in the USP throat.

All PSD data were converted in percentage of the cumulative undersize fraction CF with relation to the cut-off diameters of the cascade impactor, e.g., CF(5.8 micrometer) means the fraction in percentage of a particle ensemble with diameters less or equal than 5.8 micrometer. The PSD and the characteristic aerosol parameters $D_{50}$ sigma g and Fine Particle Fraction (<5.8 µm) (FPF) measured with the two particle size detection methods were evaluated qualitatively (visual assessment) and quantitatively by means of a significance analysis (F test, t-test, confidence intervals) (Sachs, L. 2002. Angewandte Statistik; Springer Verlag; 2002, p. 178-216). The geometric standard deviation sigma g is given by:

$$\sigma_g = \left[\frac{\sum n_i(\ln d_i - \ln d_g)^2}{N-1}\right]^{1/2} \quad d_g = (d_1 \ldots d_N)^{1/N} \qquad \text{Equation 1}$$

$n_i$: number of particles with diameter $d_i$

N: total number of particles $d_g$: geometric particle diameter

Under the prerequisite of a log-normal distribution (the logarithm of the particle diameters is normal distributed) the geometric standard deviation is equal to:

$$\sigma_g = \frac{D_{84}}{D_{50}} = \frac{D_{50}}{D_{16}} = \left[\frac{D_{84}}{D_{16}}\right]^{1/2} \qquad \text{Equation 2}$$

Equation 2 is used for calculating sigma g. $D_{50}$ is the median diameter, $D_{16}$ and $D_{84}$ are the diameters at which the cumulative size distribution reaches 16% and 84% respectively.

The results of the reticle measurements are shown in Table 1. In order to obtain representative results, seven measurements per laser diffraction analyser at different reticle positions were performed. The results of the test analyser, which was used for all subsequent investigations, show excellent correspondence to the reference analyser results. All nominal values are slightly but significantly (level of significance alpha=0.05) higher than the measured ones.

TABLE 1

PSD of a reticle measured with two laser diffraction analysers of the same type (test analyser and reference analyser). The mean values of $D_{10}$, $D_{50}$ and $D_{90}$ are compared with the nominal value.

| | Test analyser (n = 7) | Reference analyser (n = 7) | Nominal value |
|---|---|---|---|
| $D_{10}$ [μm] ± SD | 27.49 ± 0.84 | 27.61 ± 0.47 | 30.61 |
| $D_{50}$ [μm] ± SD | 36.85 ± 1.58 | 36.91 ± 1.16 | 39.05 |
| $D_{90}$ [μm] ± SD | 47.03 ± 2.12 | 47.54 ± 2.48 | 49.69 |

Since the reticle spot diameters are quite large it is reasonable to control the reliability of the laser analyser in a size range less than IO micrometer. No reticle was available in this size interval. Therefore an aerosol generator was used. The characteristic parameters of the monodisperse PSD generated by the MAG-201 10 aerosol generator are presented in Table 2. Three different boiler temperatures and hence three PSD were investigated simultaneously with the laser diffraction apparatus and the cascade impactor. The cascade impactor served as the reference test method.

TABLE 2

PSD of a monodisperse test aerosol of DEHS. The particle size was tuned by the temperature T. For each temperature at least eight measurements were performed.

| | | Laser Diffraction (n ≥ 8) | Cascade Impaction (n ≥ 8) |
|---|---|---|---|
| T = 180° C. | $D_{50}$ ± SD [micron] | 1.92 ± 0.10 | T = 180° C. |
| | Sigma g ± SD | 1.17 ± 0.32 | |
| T = 210° C. | $D_{50}$ ± SD [micron] | 3.33 ± 0.18 | T = 210° C. |
| | Sigma g ± SD | 1.16 ± 0.08 | |
| T = 240° C. | $D_{50}$ ± SD [micron] | 6.03 ± 0.30 | T = 240° C. |
| | Sigma g ± SD | 1.19 ± 0.07 | |

The $D_{50}$ values for the 210° C. and 240° C. boiler temperature show differences from 0.4 μm to 0.6 μm between the two detection methods. The $D_{50}$ value for the 180° C. boiler temperature and all geometric standard deviations are statistically equal.

Figure 11:
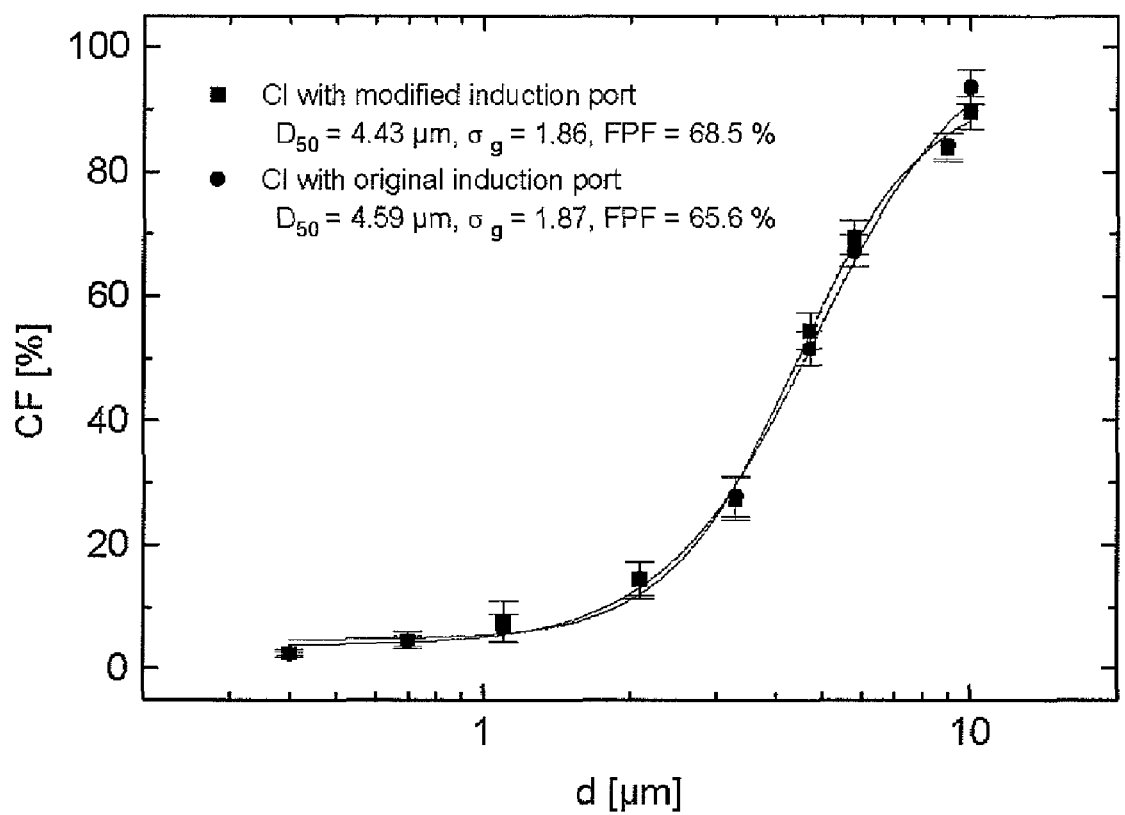
FIG. 11 shows cumulative undersize fraction in dependence of the cut-off diameters (the full lines are sigmoidal fits, and Formulation C (c=0.833%) was used).

The original induction port was modified and the usual position of the impactor was changed during the simultaneous measurements with laser diffraction and cascade impactor. These modifications do not distort the PSD, as shown in FIG. 11. The cumulative fraction curves strongly overlap and justify the use of the modified throat for the correlation studies. For the experiment the Formulation C with the highest concentration (c=0.833%) was used and all measurements were performed under saturated air conditions (RH >90%).

Figure 12:
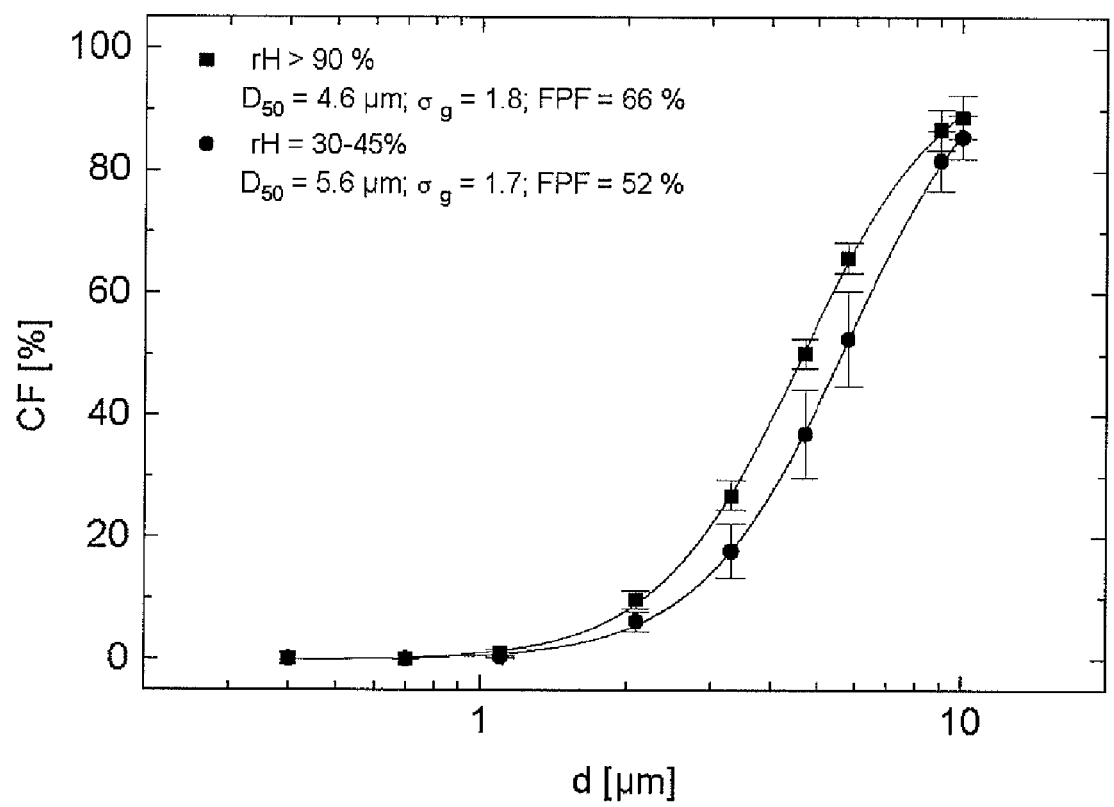
FIG. 12 shows the RH of the air influences the laser diffraction results, where the detected FPF(<5.8 μm) value increases and the $D_{50}$ decreases with decreasing humidity (Formulation C (c=0.833%) was used).

The humidity of the air strongly affects the PSD of aqueous aerosols measured with the cascade impactor. Due to evaporation the size distribution is shifted to smaller particles if RH is reduced. Even if the laser diffraction method was used, where evaporation should not play such a dominant role as for the cascade impactor because of shorter times of flight, the PSD depends also on the relative humidity of the ambient air. This is presented in FIG. 12. The data relate to laser diffraction measurements on Formulation C with the highest drug concentration (c=0.833%). The flow rate was 28.3 L/min.

Figure 13:
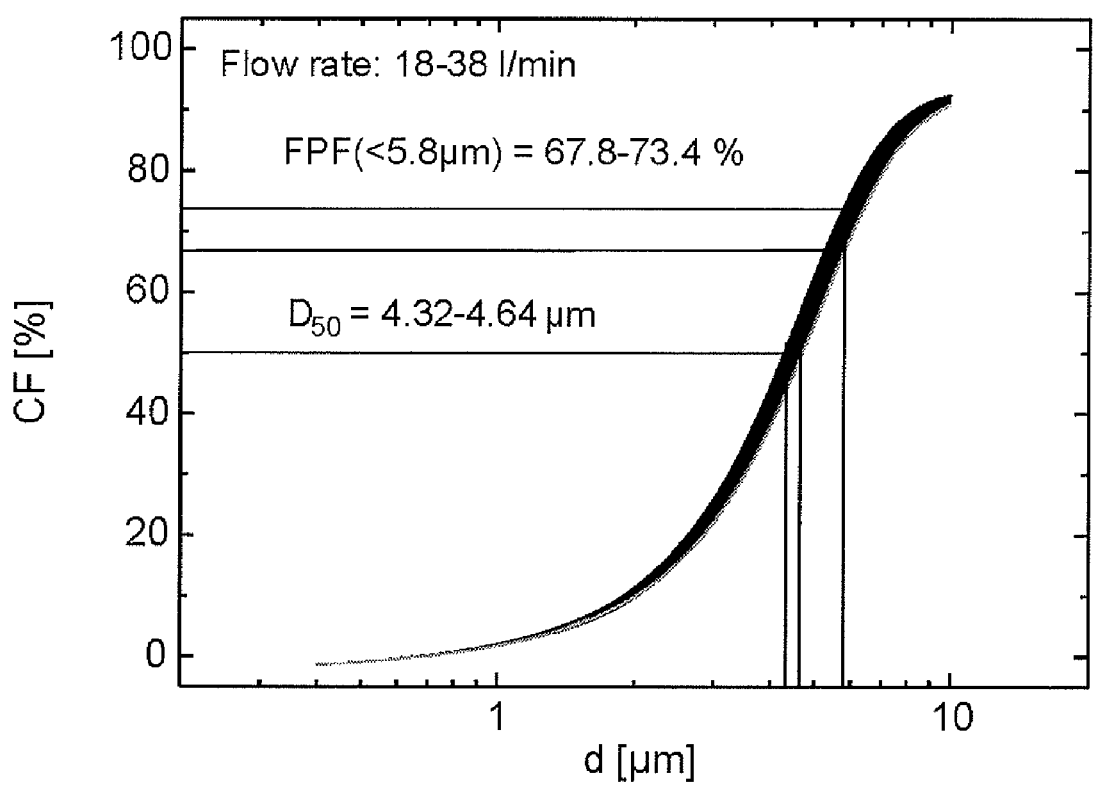
FIG. 13 shows Cumulative Fraction (CF) versus particle diameter measured by LD, where the flow rate was varied between 18 l/min and 38 l/min and the black area covers all CF curves for all flow rates (Formulation C (c=0.833%) under saturated air conditions).

The PSD was investigated by laser diffraction for different flow rates and under saturated air conditions (FIG. 13).

The flow rate was varied between 18 L/min and 38 L/min. The black area in FIG. 13 covers the corresponding cumulative fraction curves. No systematic dependence was established between the flow rate and the $D_{50}$ values or FPF respectively. The measurements were performed with the Formulation C with concentration c=0.833% under saturated air conditions.

In order to investigate the influence of the glass window position at the induction port, two induction ports were used. One port had the windows in front of the bend (FIG. 10a) another port had the windows behind the bend (FIG. 10b). The measurements were performed with the Formulation C with concentration c=0.833% under saturated air conditions. The characteristic aerosol parameters are presented in Table 3. The $D_{50}$ values are statistically equal (alpha=0.05) and the Fine Particle Fraction (FPF(<5.8 μm)) values show overlapping error bands. The geometric standard deviation is larger for the LD method which is however not systematic as one can see from the sigma g value in Table 2 related to the DEHS boiler temperature T=180° C.

TABLE 3

Characteristic aerosol parameters simultaneously measured with ACI and LD. The induction port windows were positioned behind the bend of the USP throat. The results are based on six measurements. Formulation C (c = 0.833%) was used.

| | ACI (n = 6) | LD (n = 6) |
|---|---|---|
| $D_{50}$ ± SD [micron] | 4.17 ± 0.26 | 4.12 ± 0.15 |
| Sigma g ± SD | 1.61 ± 0.04 | 1.73 ± 0.04 |
| FPF(<5.8 μm) ± SD [%] | 77.2 ± 2.5 | 74.2 ± 1.9 |

Figure 14:
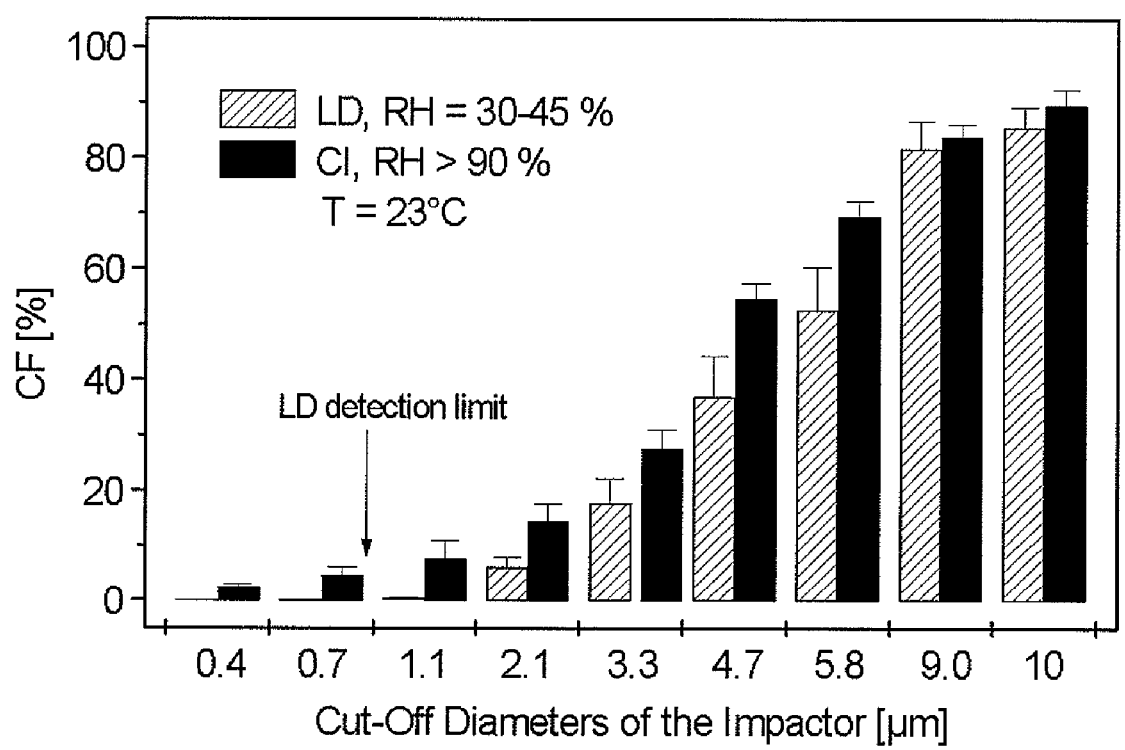
FIG. 14 shows a comparison of the Cumulative Fraction (CF) for different measurement conditions (ACI versus LD and RH >90% versus RH≈30-45%) (the distributions were not measured simultaneously, and Formulation C (c=0.833%) was used).

The motivation for the present comparison between ACI and LD is best illustrated by FIG. 14. It shows the particle size distributions for Formulation C, measured separately with the cascade impactor at RH >90% and the laser diffraction method under ambient conditions. The cumulative fractions differ significantly from each other for diameters less than 9 micrometer. A detection of particles below 1 micrometer was hardly possible with LD.

The best way to investigate the correlation of two PSD analysers is the simultaneous measurement of the particle size distribution with both methods. The correlation studies were performed at RH >90% (measurement of RH behind the impactor) and at a flow rate of 28.3 L/min for all drug formulations. The modified induction port having the inlet and outlet windows for the laser beam in front of the bend (FIG. 10a) was used. The experimental set-up is depicted in FIG. 9. In the FIGS. 15 to 17, the histograms illustrate the PSD correlation between the LD and ACI method.

Figure 15:
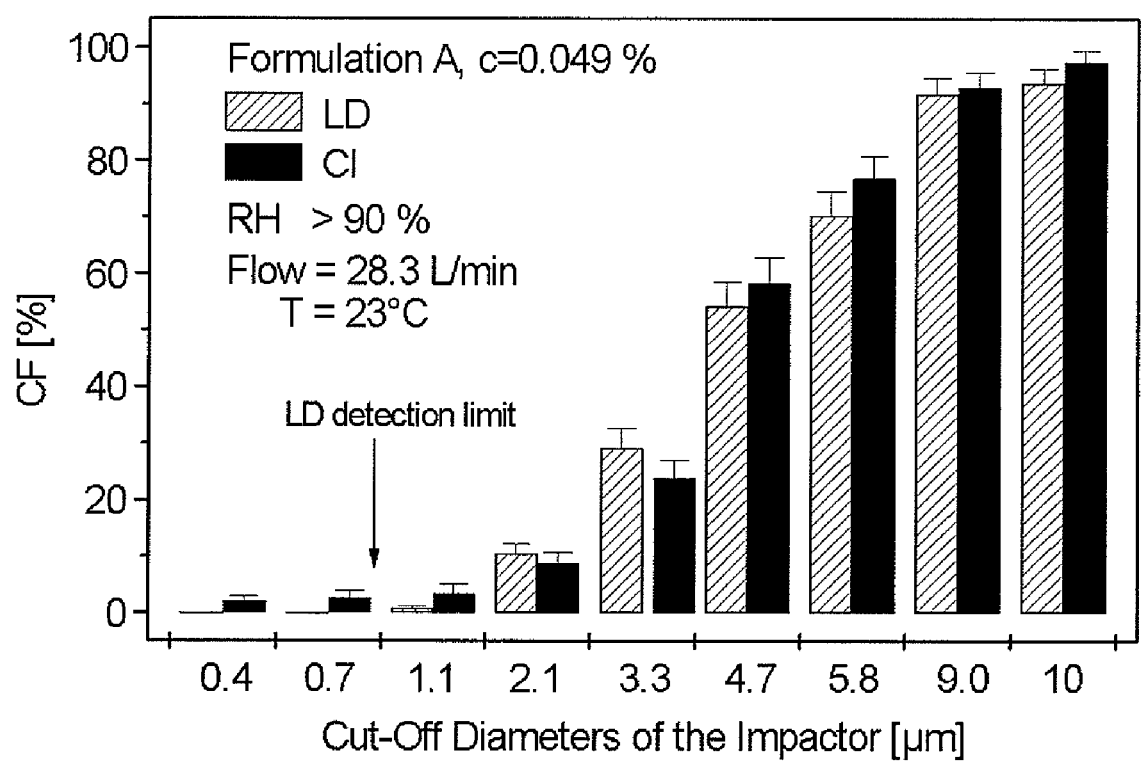
FIG. 15 shows Cumulative Fraction (CF) versus the cut-off diameters of the ACI for the Formulation A (c=0.049%).
Figure 16:
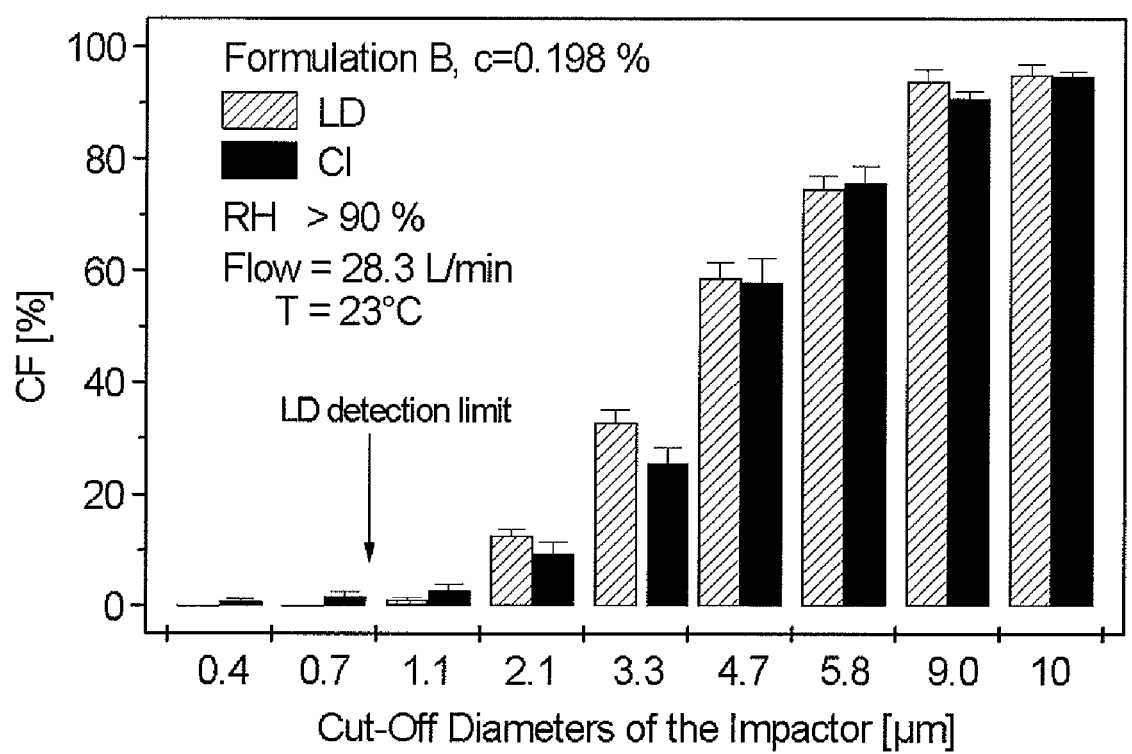
FIG. 16 shows Cumulative Fraction (CF) versus the cut-off diameters of the ACI for the formulation B (c=0.198%).
Figure 17:
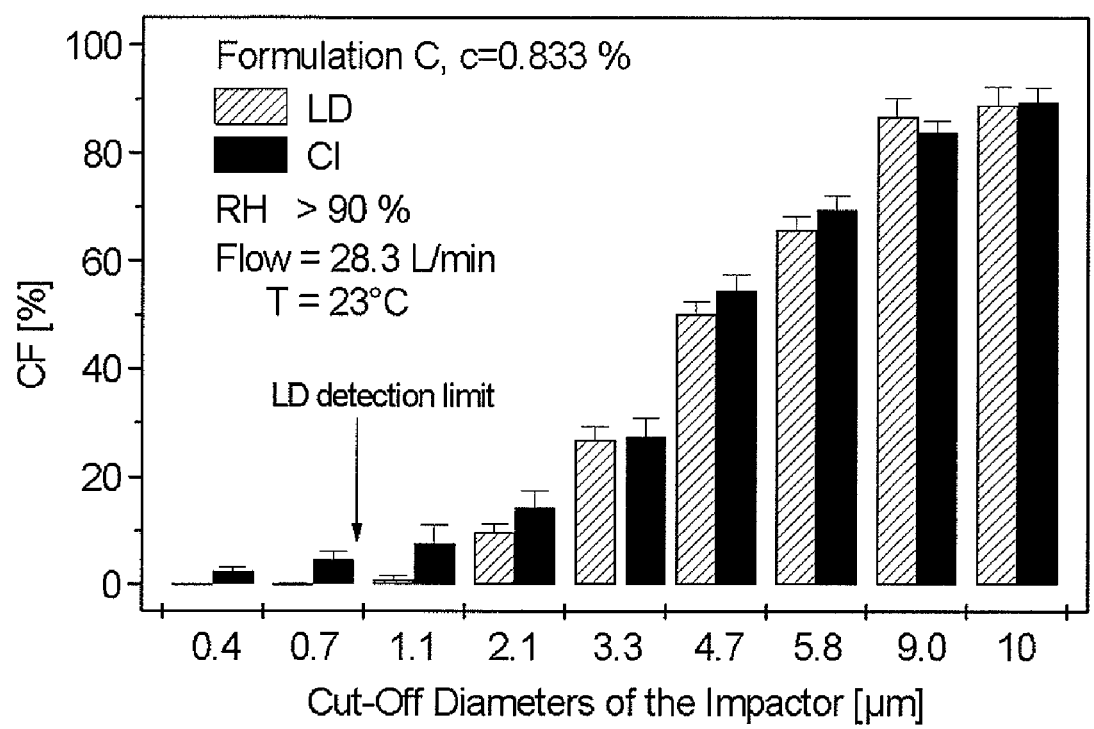
FIG. 17 shows Cumulative Fraction (CF) versus the cut-off diameters of the ACI for the Formulation C (c=0.833%).

FIGS. 15 to 17 show an excellent correspondence between the LD and the ACI results. This is definitively due to the fact that the PSD was measured simultaneously under defined conditions, i.e., constant flow rate and saturated air, in contrast to the measurement presented in FIG. 14. Table 4 summarises the corresponding characteristic aerosol parameters $D_{50}$, sigma g and FPF(<5.8 μm).

TABLE 4

D$_{50}$, sigma g and FPF (<5.8 μm) for the different Formulations A, B, C.

| | Formulation A (c = 0.049%) | | Formulation B (c = 0.198%) | | Formulation C (c = 0.833%) | |
|---|---|---|---|---|---|---|
| | ACI (n = 17) | LD (n = 17) | ACI (n = 18) | LD (n = 18) | ACI (n = 13) | LD (n = 12) |
| CF$_{[0\ micron;\ 1.1\ micron]}$ [%] | 4.37 ± 0.24 | 4.42 ± 0.24 | 4.34 ± 0.18 | 4.16 ± 0.14 | 4.43 ± 0.19 | 4.59 ± 0.17 |
| CF$_{[1.1\ micron;\ 4.7\ micron]}$ [%] | 1.52 ± 0.05 | 1.72 ± 0.05 | 1.57 ± 0.03 | 1.72 ± 0.03 | 1.86 ± 0.14 | 1.76 ± 0.04 |
| CF$_{[4.7\ micron;\ 10\ micron]}$ [%] | 76.9 ± 4.0 | 69.7 ± 3.9 | 74.4 ± 2.9 | 73.8 ± 2.5 | 68.5 ± 2.3 | 66.2 ± 2.7 |

In Table 5 the different cut-off points of the ACI are summarised in three size intervals from [0 micrometer; 1.1 micrometer], [1.1 micrometer; 4.7 micrometer] and from [4.7 micrometer; 10 micrometer]. The corresponding cumulated fractions CF are compared for the ACI and LD method. Except for the [0 micrometer; 1.1 micrometer] interval good equivalence between the ACI and LD method can be found. The higher CF values of the ACI evaluation in comparison to the LD for the [0 micrometer; 1.1 micrometer] interval are caused by the detection limit of the LD.

TABLE 5

Cumulative fraction of ACI and LD for different size intervals.
Additionally the 1σ standard deviation is shown.

| | Formulation A (c = 0.049%) | | Formulation B (c = 0.198%) | | Formulation C (c = 0.833%) | |
|---|---|---|---|---|---|---|
| | ACI (n = 17) | LD (n = 17) | ACI (n = 18) | LD (n = 18) | ACI (n = 13) | LD (n = 12) |
| CF$_{[0\ micron;\ 1.1\ micron]}$ [%] | 3.31 ± 2.71 | 0.94 ± 0.31 | 2.75 ± 1.69 | 1.06 ± 0.23 | 7.63 ± 4.03 | 0.86 ± 0.68 |
| CF$_{[1.1\ micron;\ 4.7\ micron]}$ [%] | 54.95 ± 7.24 | 53.24 ± 6.69 | 55.25 ± 6.61 | 57.67 ± 4.67 | 46.83 ± 7.79 | 49.27 ± 4.68 |
| CF$_{[4.7\ micron;\ 10\ micron]}$ [%] | 39.16 ± 8.62 | 39.54 ± 8.85 | 36.69 ± 6.37 | 36.40 ± 5.50 | 35.02 ± 6.29 | 38.69 ± 7.31 |

The laser diffraction analyser worked reliable. No significant difference was established between the analyser and a reference analyser of the same type by measuring the well-defined size distribution of a reticle. The deviations of the results from the nominal values provided by the manufacturer are possibly caused by the static feature of the reticle, which is only under special prerequisites a suitable model for a moving particle system (Müthlenweg, H; E. D. Hirleman. 1999. Reticles as Standards in Laser Diffraction Spectroscopy. Part. Part. Syst. Charact. 16:47-53). The ACI and LD method show satisfactory equivalence in respect to the generated reference particle distributions. The small differences appeared mainly due to the calibration uncertainty of the impaction plates or of the software calibration (see Table 1). The calibrations differ in some respect from the manufacturers' calibration, but are sufficiently consistent with theory. The investigation of the impaction plate calibration is described by Nichols, S. C. 2000. Andersen Cascade Impactor: Calibration and Mensuration Issues for the Standard and Modified Impactor. PharmEuropa; 12(4): 584-588 and Vaughan, N. P. 1989. The Andersen Impactor: Calibration, Wall Losses and Numerical Simulation. Journal of Aerosol Science 20(1): 67-90. Data reduction methods for the evaluation of cascade impactor results are discussed recently by O'Shaughnessy, P. T., O. G. Raabe. 2003. A Comparison of Cascade Impactor Data Reduction Methods. Journal of Aerosol Science and Technology 37: 187-200. The sharp distribution (sigma g<1.15 according to the specification) of the aerosol PSD generated with the MAG-2010 PALAS aerosol generator enhances the sensitivity against calibration differences.

Figure 18:
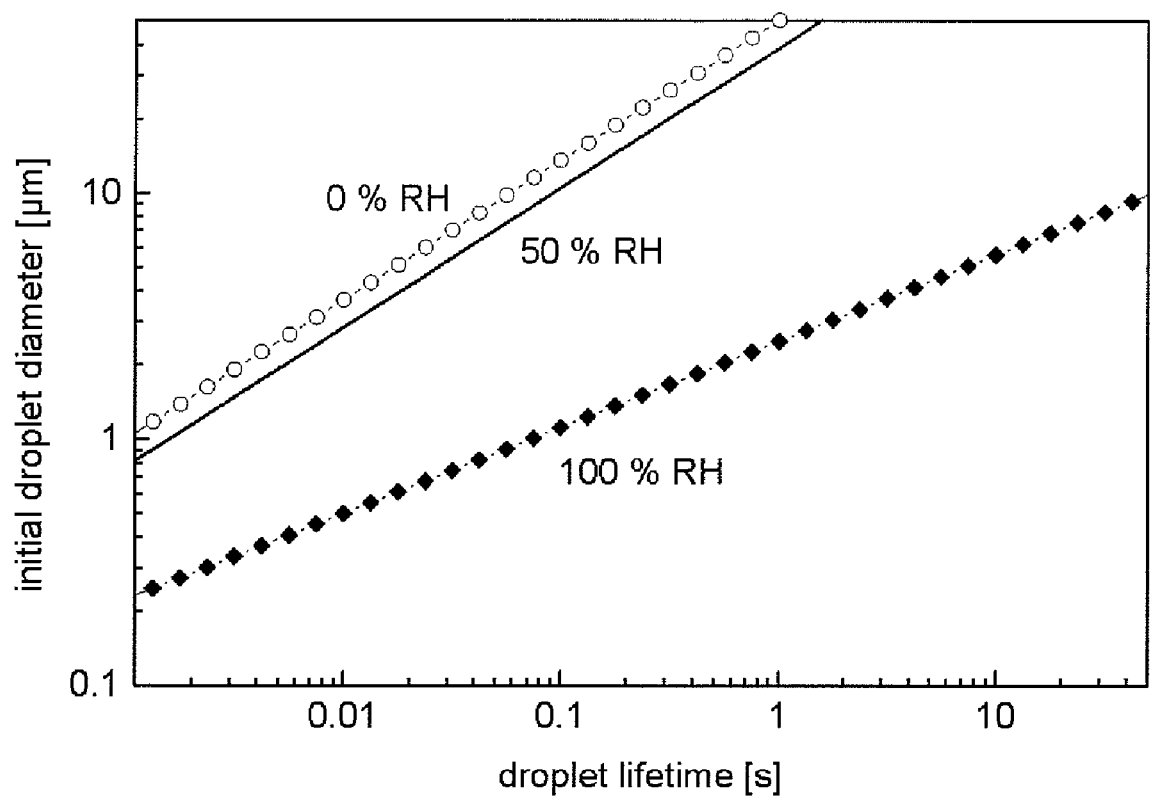
FIG. 18 shows water droplet lifetimes as a function of droplet size for 0, 50 and 100% relative humidity at 20° C. (after Hinds (1982)).

At a first glance one might assume that the evaporation of aqueous aerosol droplets does not influence the PSD if the fast LD method is used. However according to FIG. 18 (after Hinds, W. C. 1982. Aerosol Technology: Properties, Behaviour, and Measurement of Airborne Particles. John Wiley & Sons. 270), the lifetime of aqueous droplets with particle diameters between 1 micrometer and 10 micrometer is in the millisecond range for RH<50%.

The time of flight of the aqueous droplets from the nozzle to the laser beam is also in the millisecond range as can be calculated from the velocity of the aerosol cloud and the nozzle laser beam distance by a time of flight approximation. Therefore, the evaporation of the aqueous droplets cannot be neglected during the laser diffraction measurements. The finite droplet lifetime even for RH=100% (cf. FIG. 18) is caused by the curvature of the droplets. At curved surfaces the vapour pressure is higher than at smooth surfaces due to larger mean distance of the neighbouring particles. The attractive interaction is therefore reduced. Further the particle shrinkage is non-linear, i.e., the smaller the initial particles are, the faster is the shrinkage rate. This evaporation behaviour in connection with the detection limit of the configuration of the LD apparatus may explain the situation in FIG. 12. It shows the unexpected situation that for LD at reduced relative humidity the detected FPF(<5.8 μm) became smaller. Concomitantly, the D$_{50}$ value increased. This observation at RH about 30-45% can be explained by a fast evaporation of the droplets which reduces the size of the smaller droplets below the detection threshold of the LD device. A comparison of LD and ACI will fail at low relative humidity if the measurement range is not adapted to the dried droplets. On the other hand, at RH>90% the particles are relatively stable in size. Thus, at almost saturated conditions the measured PSD represents the original one better and leads to $D_{50}$ and FPF(<5.8 μm) values which are stable in time and which are in good agreement with the impactor values.

Figure 19:
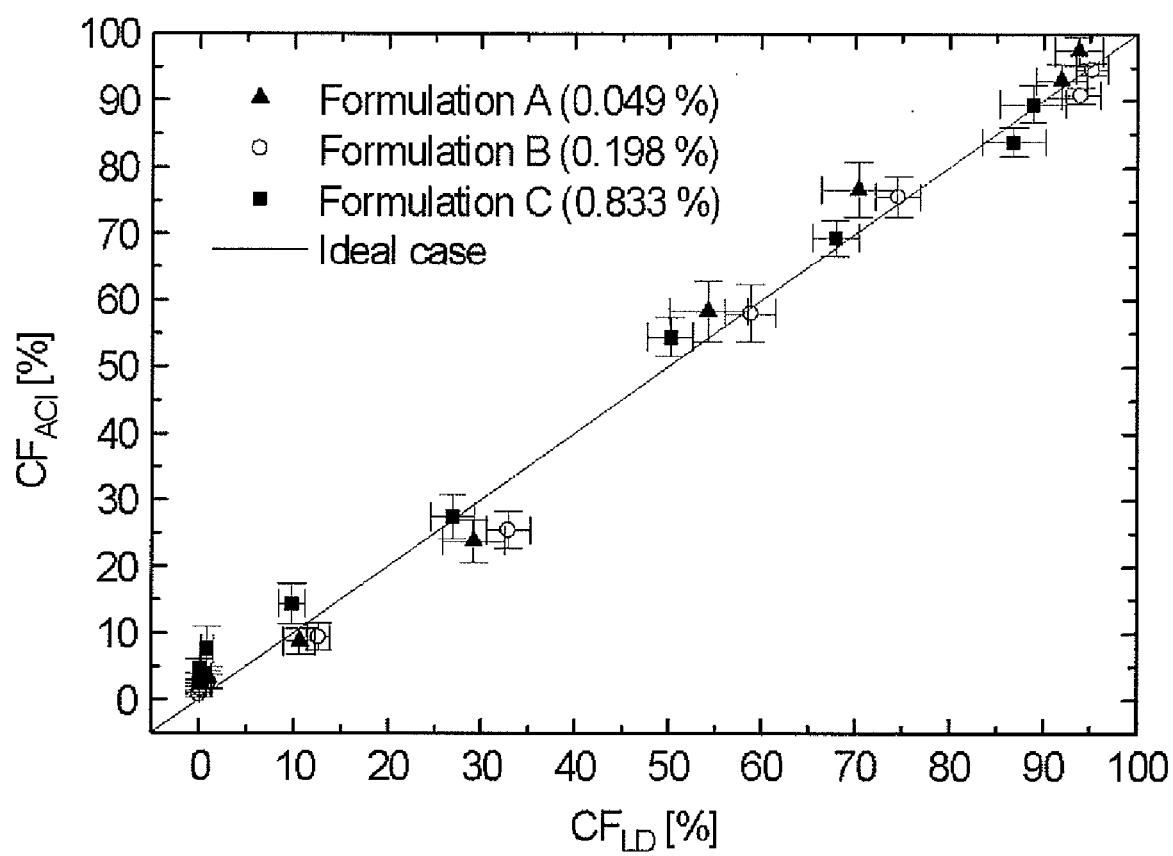
FIG. 19 shows Cumulative Fraction (CF) measured with the ACI in dependence of the Cumulative Fraction (CF) measured with LD, where the experimental data represent the respective cut-off points of the ACI (i.e. the CF values for the 0.4, 0.7, 1.1, 2.1, 3.3, 4.7, 5.8, 9.0 and 10.0 micrometer cut-off sizes) and each formulation is dosed to the ideal case (straight line) where $CF_{ACI}$ and $CF_{LD}$ should be equal.

In FIG. 19, a direct comparison is made between the cumulated fractions measured with LD and ACI is presented for the investigated formulations at RH>90%. The correlation between the ACI and LD method is satisfactory. Almost all data points are positioned dose to the ideal line. The higher cumulative fraction of the ACI at cut-off sizes below 1 micrometer is caused by the detection limit of the lens. Other factors that influence the correlation are the beam diameter, possibly scattered light from the surroundings and eventually the evaluation software. The beam diameter is 2.2 mm and therefore only a part of the aerosol cloud was illuminated by the laser beam. This part is quite representative for the PSD of the whole cloud as FIG. 19 proves, but slight deviations cannot be excluded. The choice of another lens connected with a larger beam diameter has the disadvantage to shift the detection limit to larger particle diameters. Also the cascade impactor results do not exactly represent the original PSD of the aerosol. One possible source of error is the already mentioned calibration uncertainty. The amount of aerosol deposited onto the walls of the impactor (wall losses) is usually only 2-3% for the Respimat® device and was therefore neglected in the data evaluation. However, according to the investigations by Vaughan (see above), wall losses can become serious under special measurement conditions.

While the invention has been described in detail and with reference to specific embodiments thereof, it will be apparent to one skilled in the art that various changes and modifications can be made therein without departing from the spirit and scope thereof. Accordingly, it is intended that the present invention covers the modifications and variations of this invention provided they come within the scope of the appended claims and their equivalents.

What is claimed is:

1. A method for measuring the particle size distribution of a pharmaceutical aerosol by the use of laser diffraction, comprising:
generating an aerosol utilizing an inhaler;
spraying the generated aerosol into pre conditioned air having a relative humidity of at least 80%;
analyzing particle size distribution in the sprayed aerosol embedded into the pre-conditioned air using laser diffraction.

2. The method according to claim 1, wherein the pharmaceutical aerosol is an aerosol of liquid droplets.

3. The method according to claim 2, wherein the relative humidity is at least 85%.

4. The method according to claim 2, wherein the relative humidity is at least 90%.

* * * * *